US010368824B2

(12) United States Patent
Yamakawa et al.

(10) Patent No.: US 10,368,824 B2
(45) Date of Patent: Aug. 6, 2019

(54) X-RAY CT DEVICE AND PROCESSING DEVICE

(71) Applicant: HITACHI, LTD., Chiyoda-ku, Tokyo (JP)

(72) Inventors: Keisuke Yamakawa, Tokyo (JP); Shinichi Kojima, Tokyo (JP)

(73) Assignee: HITACHI, LTD., Tokyo (JP)

( * ) Notice: Subject to any disclaimer, the term of this patent is extended or adjusted under 35 U.S.C. 154(b) by 198 days.

(21) Appl. No.: 15/123,192

(22) PCT Filed: Feb. 4, 2015

(86) PCT No.: PCT/JP2015/053044
§ 371 (c)(1),
(2) Date: Sep. 1, 2016

(87) PCT Pub. No.: WO2015/137011
PCT Pub. Date: Sep. 17, 2015

(65) Prior Publication Data
US 2017/0119335 A1    May 4, 2017

(30) Foreign Application Priority Data

Mar. 14, 2014 (JP) ................................ 2014-052493

(51) Int. Cl.
*A61B 6/00* (2006.01)
*A61B 6/03* (2006.01)
*G06T 11/00* (2006.01)

(52) U.S. Cl.
CPC ............ *A61B 6/5258* (2013.01); *A61B 6/032* (2013.01); *A61B 6/461* (2013.01); *A61B 6/467* (2013.01);
(Continued)

(58) Field of Classification Search
CPC ......... A61B 6/032; A61B 6/461; A61B 6/467; A61B 6/5205; A61B 6/5258; G06T 11/003
See application file for complete search history.

(56) References Cited

U.S. PATENT DOCUMENTS

2014/0226887 A1\* 8/2014 Takahashi .............. A61B 6/032
382/131

FOREIGN PATENT DOCUMENTS

JP         2006-25868 A    2/2006
WO    WO 2012/147471 A1   11/2012

\* cited by examiner

*Primary Examiner* — Chih-Cheng Kao
(74) *Attorney, Agent, or Firm* — Miles & Stockbridge PC

(57) ABSTRACT

This X-ray CT device uses iterative reconstruction to obtain a CT image with the desired noise reduction or X-ray reduction ratio. An iterative approximation reconstruction unit (136) is provided which, from measured projection data obtained by an X-ray detection unit of the X-ray CT device, iteratively reconstructs a CT image in a reconstruction range of a subject, and iteratively corrects the CT image such that calculated projection data, calculated through forward projection of a CT image, is the same as the difference between measured projection data detected by the X-raw detection unit and calculated projection data. The iterative approximation reconstruction unit is provided with a parameter determination unit (151), an iterative correction unit (152), and a table unit (153) which calculates in advance the relation between each parameter used in the iterative reconstruction, and noise reduction or X-ray reduction ratio in the CT image. The parameter determination unit (151) determines the parameters from a calculation table in the table unit (153) depending on the desired reduction ratio.

10 Claims, 23 Drawing Sheets

(52) U.S. Cl.
CPC .......... *A61B 6/5205* (2013.01); *G06T 11/006* (2013.01); *G06T 2211/424* (2013.01)

| UPDATE FREQUENCY | RECONSTRUCTION FILTER | ... | ※ APPROXIMATION CURVE (QUADRATIC) |
|---|---|---|---|
| 20 | Ramp | ... | $y = a_1 \cdot x^2 + b_1 \cdot x + c_1$ |
| 50 | Ramp | ... | $y = a_2 \cdot x^2 + b_2 \cdot x + c_2$ |
| 20 | Shepp-Logan | ... | $y = a_3 \cdot x^2 + b_3 \cdot x + c_3$ |
| 50 | Shepp-Logan | ... | $y = a_4 \cdot x^2 + b_4 \cdot x + c_4$ |
| ... | ... | ... | ... |

※ DENOTES NOISE REDUCTION RATIO [%], y DENOTES $\beta$ RATE

CT IMAGE OF EACH
PARAMETER $\beta$ RATE b

WEIGHT W (i) OF DETECTION ELEMENT    WEIGHT IMAGE WI (j) AT EACH POSITION

WEIGHT IMAGE WI (j) AT EACH POSITION

PARAMETER β RATIO IMAGE βI (j) AT EACH POSITION

GENERALLY EMPLOYED METHOD    PROPOSED METHOD

CT IMAGE

SD IMAGE Nc (j)

IMAGE NI (j) OF NOISE REDUCTION RATIO

PARAMETER β IMAGE β1 (j)

FIG. 18A
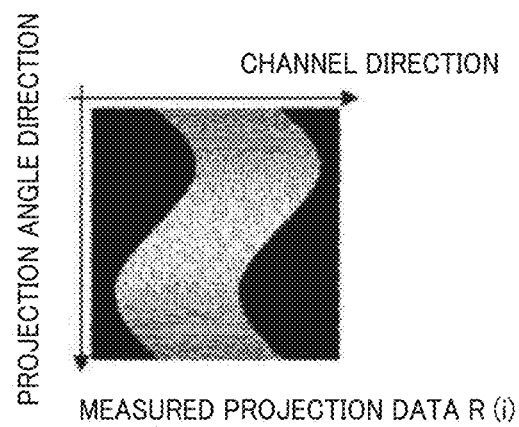
FIG. 18B
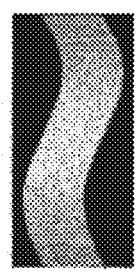 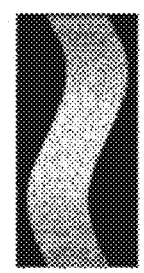
MEASURED PROJECTION DATA Rc, odd (i) OF ODD CHANNEL NUMBER
MEASURED PROJECTION DATA Rc, even (i) OF EVEN CHANNEL NUMBER

FIG. 18C
CT IMAGE $\lambda_{c,odd}(j)$ OF
ODD CHANNEL NUMBER
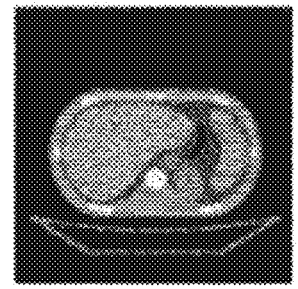
CT IMAGE $\lambda_{c,even}(i)$ OF
EVEN CHANNEL NUMBER
FIG. 18D
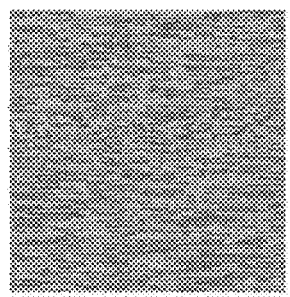
DIFFERENCE IMAGE $\Delta\lambda c(j)$
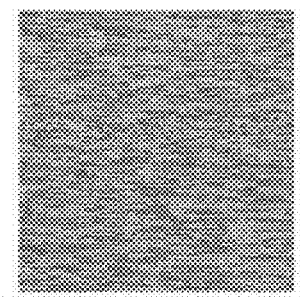
CORRECTED DIFFERENCE
IMAGE $\Delta\lambda^*c(j)$ SD IMAGE Nc (j)

CT IMAGES EACH WITH DIFFERENT OBLATENESS

NOISE REDUCTION RATIO AT EACH β RATE b

NOISE REDUCTION RATIO 50%

INITIAL IMAGE    CONTOUR INFORMATION    ACQUIREMENT OF LONG
                 AFTER EXTRACTION       DIAMETER a AND SHORT
                                        DIAMETER b

CT IMAGE

WEIGHT W (i) OF ALL PROJECTION
NUMBERS i RELATING TO PIXEL i

STANDARDIZED WEIGHT
AFTER REPLACEMENT

NOISE REDUCTION RATIO 50%

X-RAY CT DEVICE AND PROCESSING DEVICE

TECHNICAL FIELD

The present invention relates to an X-ray CT (Computed Tomography) device, and more particularly, to an iterative reconstruction technology for iteratively correcting the CT image.

BACKGROUND ART

The X-ray CT device is configured to calculate an X-ray absorption coefficient at each point in a subject body from measured projection data obtained by multidirectionally taking images of the subject, and acquire the X-ray absorption coefficient distribution image (hereinafter referred to as CT image). Generally, the X-ray absorption coefficient is replaced with a CT value standardized with air and water (air: −1000, water: 0) for diagnostic use.

The CT image is expressed by superposing tomographic planes of the subject along the body axis. The CT image is clinically useful in the medical site because the use of the CT image allows correct and instantaneous diagnosis of the patient condition. Satisfying the condition for high image quality necessary for diagnosis of the physician inevitably involves the subject in radiation exposure to a certain degree. Making efforts to reduce the X-ray dosage for low radiation exposure may increase the ratio between the detected signal and noise. As a result, linear streak artifact and granular noise which may cause diagnostic error may increasingly occur. There has been demanded establishment of both quality diagnosis and low radiation exposure by reducing the streak artifact and noise during image-taking with low radiation dose.

The iterative reconstruction method according to Patent Literature 1 discloses that the calculated projection data or the CT images are iteratively corrected in order to equalize the difference between the calculated projection data and the measured projection data so as to reduce noise. Compared with the generally employed method for analytically calculating the CT value, the iterative reconstruction method is required to cope with more problems of, for example, increase in the calculation amount resulting from repetitive updating, and need for optimization of huge amounts of parameters.

In order to establish noise reducing effect demanded by the smoothing process during updating as one of the problems, many parameters have to be set up. Patent Literature 1 employs the measured value of noise of the CT image output during the iterative correction, in other words, standard deviation (hereinafter referred to as SD) indicating dispersion in the CT values by the iterative reconstruction. The correction is continuously executed, or the parameter for the iterative reconstruction is changed for correction until the measured SD during the iterative correction reaches the required SD.

CITATION LIST

Patent Literature

PTL 1: JP-A-2006-25868

SUMMARY OF INVENTION

Technical Problem

The technique as disclosed in Patent Literature 1 for acquiring the SD, it is necessary to measure the SD from the CT image during the iterative correction. As it is necessary to set the region of interest (hereinafter referred to as ROI) in the tissue constituted by the uniform CT value for the measurement, it is difficult to accurately measure the SD in the tissue constituted by different CT values.

It is an object of the present invention to provide an X-ray CT device and a processing device which are capable of determining the iterative reconstruction parameters for achieving the desired reduction ratio.

Solution to Problem

In order to establish the aforementioned object, the present invention provides an X-ray CT device having an X-ray generation unit for generating X-ray, an X-ray detection unit for detecting the X-ray after transmitting through a subject to acquire measured projection data, an image-taking unit that includes a mechanism provided with the X-ray generation unit and the X-ray detection unit, and rotates around the subject, and an image generation unit that includes an iterative approximation reconstruction unit for iteratively correcting a CT image generated by the image-taking unit from the measured projection data so as to substantially equalize a difference between calculated projection data acquired by a forward projection calculation from the CT image and the measured projection data. The image generation unit includes a table unit that stores a relationship between a noise or an X-ray reduction ratio of the CT image and a parameter used for iterative correction. The iterative approximation reconstruction unit determines the parameter from the table unit in accordance with the noise or the X-ray reduction ratio of the CT image.

In order to establish the aforementioned object, the present invention further provides a processing device including at least a processing section and a storage section. The processing section includes an image generation unit provided with an iterative approximation reconstruction unit for iteratively correcting a CT image generated from measured projection data acquired by an X-ray CT device so as to substantially equalize a difference between calculated projection data derived from the CT image by a forward projection calculation and the measured projection data. The storage section stores a relationship between a noise or an X-ray reduction ratio of the CT image, and a parameter used for iterative correction. The iterative approximation reconstruction unit determines the parameter from the relationship stored in the storage section in accordance with the noise or the X-ray reduction ratio of the CT image.

Advantageous Effects of Invention

The present invention is configured to allow determination of iterative reconstruction parameters for achieving the desired reduction ratio without depending on CT image conditions such as the system configuration before and during iterative correction.

BRIEF DESCRIPTION OF DRAWINGS

FIG. 18A is a view showing an example of measured projection data for explaining the result of calculation performed by the noise calculation unit according to the fourth embodiment.

FIG. 18B is a view showing examples of measured projection data of odd/even channels for explaining results of calculation performed by the noise measurement unit according to the fourth embodiment.

FIG. 18C is a view showing examples of the CT images of the odd/even channels for explaining results of calculation performed by the noise measurement unit according to the fourth embodiment.

FIG. 18D is a view showing examples of difference image and corrected difference image for explaining results of calculation performed by the noise measurement unit according to the fourth embodiment.

DESCRIPTION OF EMBODIMENT

Figure 1:
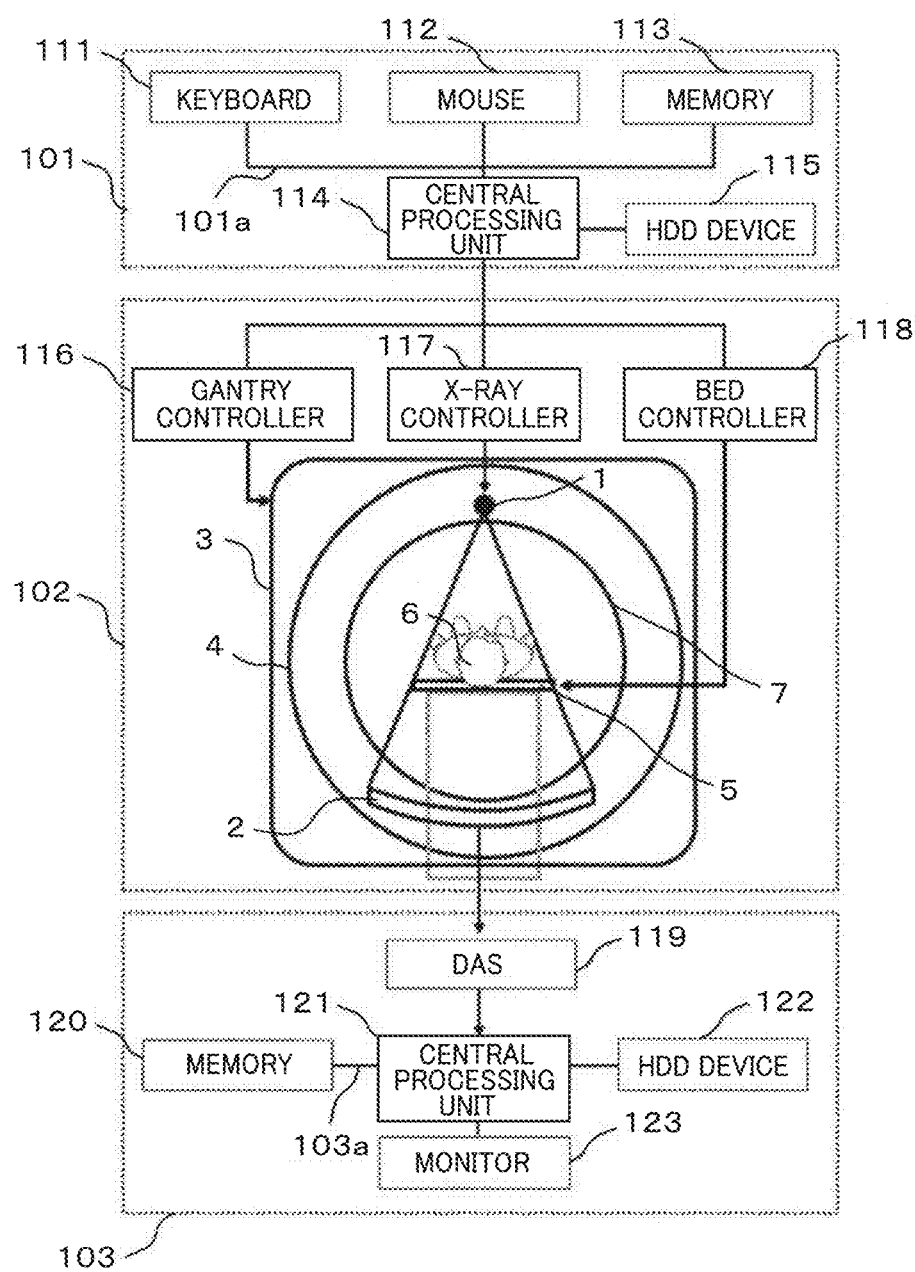
FIG. 1 is a block diagram explaining a hardware structure of the respective components of the X-ray CT device according to a first embodiment.

Embodiments of the present invention will be described sequentially referring to the drawings.

First Embodiment

Figure 2:
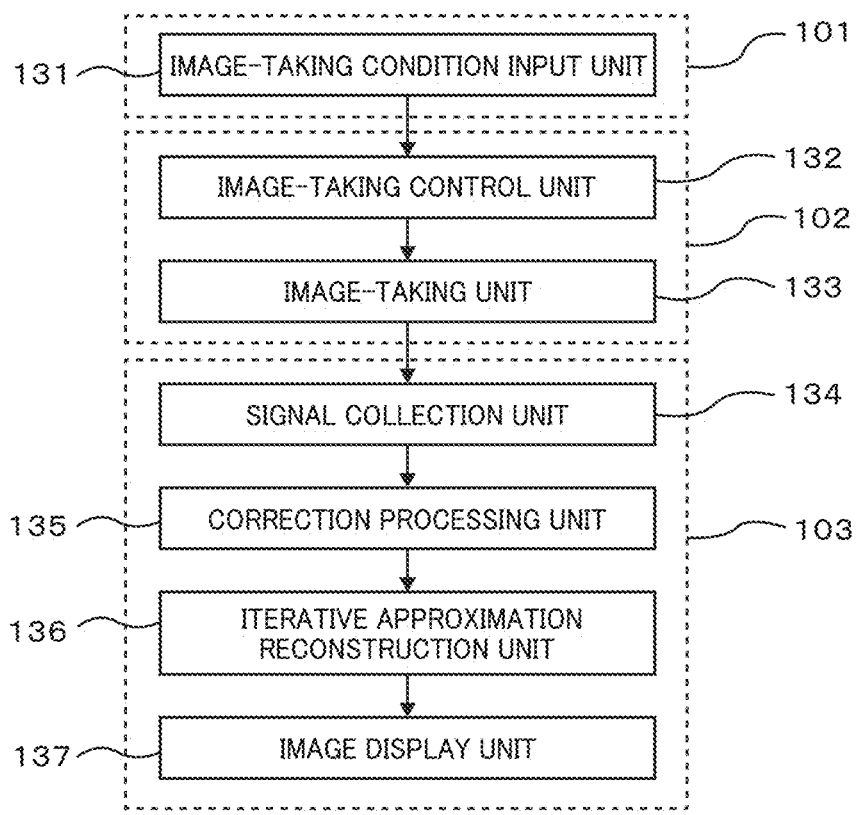
FIG. 2 is a functional block diagram of the X-ray CT device according to the first embodiment.

FIG. 1 is a view showing a hardware structure of an X-ray CT device according to a first embodiment. FIG. 2 is a functional block diagram showing functions of the X-ray CT device according to the first embodiment. The X-ray CT device according to the embodiment includes an image-taking section 102 and an image generation section 103. The image-taking section 102 includes an X-ray generation unit 1 for generating X-ray, an X-ray detection unit 2 for detecting the X-ray after transmitting through the subject to acquire measured projection data, and a mechanism having the X-ray generation unit and the X-ray detection unit installed, which rotates around the subject. The image generation section 103 includes an iterative reconstruction unit 136 that generates the CT image based on the measured projection data from the image-taking section, and iteratively corrects the CT image so as to equalize the difference between the calculated projection data obtained by a forward projection calculation from the CT image, and the measured projection data. The image generation section includes a table unit 153 for storing the relationship between the reduction ratio of noise or X-ray of the CT image, and parameters used for the iterative correction. The iterative approximation reconstruction unit determines the parameter from the table unit in accordance with the reduction ratio of noise or X-ray of the CT image.

As FIG. 1 clearly shows, the X-ray CT device according to the embodiment includes an input section 101, the image-taking section 102, and the image generation section 103. The image-taking section 102 includes the X-ray generation unit 1 for generating X-ray, the X-ray detection unit 2 for detecting X-ray after transmitting through the subject to acquire the measured projection data, a gantry 3, a rotary plate 4 that has the X-ray generation unit 1 and the X-ray detection unit 2 mounted, and rotates around the subject, an image-taking unit 133 having a circular opening 7 through which a bed 5 on which a subject 6 lies is inserted, and an image-taking control unit 132 including a gantry controller 116, an X-ray controller 117, and a bed controller 118. The gantry controller 116 controls rotating operations of the rotary plate 4. The X-ray controller 117 controls operations of the X-ray generation unit 1. The bed controller 118 controls the position of the bed 5. The hardware structures of the input section 101 and the image generation section 103 will be described later.

Referring to FIG. 2, the image generation section 103 according to the embodiment is constituted by functional blocks of a signal collection unit 134, a correction processing unit 135, the iterative approximation reconstruction unit 136, and an image display unit 137. The iterative approximation reconstruction unit 136 is configured to reconstruct the CT image in the reconstruction range of the subject from the measured projection data acquired by the X-ray detection unit 2 constituted by the X-ray detector, and to acquire the calculated projection data by projection calculation of the CT image in the forward direction (hereinafter referred to as forward projection calculation). Then the CT image is iteratively corrected so as to equalize the difference between the acquired calculated projection data and the measured projection data.

The iterative approximation reconstruction unit 136 determines the parameter used for iterative reconstruction in order to acquire the CT image that achieves the desired noise reduction ratio or X-ray reduction ratio. This embodiment acquires the table that contains data of preliminarily calculated noise reduction ratio or the X-ray reduction ratio of the CT image in accordance with the respective parameters. Upon generation of the image, the CT image is iteratively corrected by using the parameter of the table determined in accordance with the desired reduction ratio.

As described above, the X-ray CT device according to the embodiment introduces the parameter determined from the preliminarily calculated table to the iterative reconstruction so as to ensure acquisition of the CT image that achieves the desired noise reduction ratio or the X-ray reduction ratio.

In the embodiment, the noise reduction ratio refers to the one expressed as a percentage of noise reduction of the CT image after the iterative correction on the basis of noise of the CT image which has been reconstructed (hereinafter referred to as an initial image) by the analytical reconstruction process such as the known Feldkamp method.

[Formula 1]

$$\text{noise reduction ratio}[\%] = (1 - \text{image noise after iterative correction/initial image noise}) \cdot 100 \qquad (1)$$

Meanwhile, the X-ray reduction ratio in the embodiment refers to the ratio of the reduceable X-ray expressed as a percentage by the iterative reconstruction under the condition for acquiring the image quality equivalent to that of the CT image reconstructed by using the aforementioned analytical reconstruction method. In the embodiment, the image quality is explained in reference to the SD indicating noise in the arbitrary region. However, it is possible to use another evaluation index such as spatial resolution. The X-ray reduction ratio may be expressed by the following formula (2) because the X-ray amount can be converted from the SD approximately.

[Formula 2]

$$\text{X-ray reduction ratio}[\%] = (1 - \text{image noise after iterative correction/initial image noise})^2 \cdot 100 \qquad (2)$$

Since the noise reduction ratio and the X-ray reduction ratio may be converted through the formulae (1) and (2), respectively, the noise reduction ratio will only be described hereinafter while omitting description of the X-ray reduction ratio.

In the description of the X-ray CT device according to the embodiment, the subject refers to the one having its image taken, and contains a subject 6, and the bed 5 which supports the subject 6. The subject 6 is not limited to a human body, but may be an inanimate body to be inspected, for example, phantom and machinery.

The iterative approximation reconstruction unit 136 includes an iterative correction unit configured to correct the CT image by using the difference between the measured projection data and the calculated projection data for equalization (hereinafter referred to as Likelihood calculation), and to correct the CT image by using the value calculated from the CT value difference between two or more pixels of the CT image before correction for reducing the CT value difference (hereinafter referred to as Prior calculation), which are repeatedly performed. In the embodiment, the parameter determined from the preliminarily calculated table is used as the coefficient for the Prior calculation in order to acquire the CT image which achieves the desired noise reduction ratio. At this time, the parameter may be used as the coefficient of the Likelihood calculation in place of the one for the Prior calculation.

The X-ray CT device according to the first embodiment will be described further specifically referring to the drawings. FIG. 1 is a view showing the hardware structure of the X-ray CT device according to the first embodiment. As described later, the iterative approximation reconstruction unit 136 of the image generation section 103 is installed in the X-ray CT device as software. FIG. 2 is a functional block diagram of the X-ray CT device to be realized by the respective types of software.

As generally described as above, the X-ray CT device of the embodiment includes the input section 101 for inputting the image-taking condition such as the X-ray radiation condition, and the image reconstruction condition, the image-taking section 102 for outputting the measured projection data by controlling the image-taking, X-ray radiation and detection, and the image generation section 103 that performs correction and image reconstruction with respect to the measured projection data as the detected signal so as to output the image. The input section 101 and the image generation section 103 are not necessarily integrated with the main body device provided with the image-taking section 102. Those sections may be disposed apart from the image-taking section 102, and remotely connected thereto via network. In such a case, the image generation section 103 may be configured as an independent processor for processing the measured projection data.

The input section 101 having the hardware structure for the general purpose computer includes a keyboard 111 and a mouse 112 each as an input-output unit, a memory 113 and an HDD device 115 each as a storage unit, and a central processing unit 114 as the processor. The image generation section 103 includes a DAS 119, a memory 120 as the storage unit, a central processing unit 121 as the processor, an HDD device 122 as the storage unit, and a monitor 123 as the display unit. Each of the input section 101 and the image generation section 103 may be configured to be an independent hardware, or commonly used hardware.

As FIG. 2 shows, the input section 101 functions as an image-taking condition input unit 131 for inputting the image-taking condition. The image-taking section 102 functions as the image-taking control unit 132 for controlling the image-taking operation based on the image-taking condition input by the image-taking condition input unit 131, and the image-taking control unit 133 for irradiation and detection of X-ray. The image generation section 103 functions as the signal collection unit 134 for converting the detected signal into the digital signal, the correction processing unit 135 for correcting the digital signal, the iterative approximation reconstruction unit 136 for image reconstruction of the corrected projection data, and the image display unit 137 for outputting the reconstructed CT image. The signal collection unit 134 for AD conversion is disposed in the image-taking section 102 which is configured to ensure output of the measured projection data as the digital signal, and preferably to be connected to the image generation section 103 via the network.

As FIG. 1 shows, the input section 101 includes the keyboard 111 and the mouse 112 for inputting the image-taking condition. It is also possible to provide the other input unit such as the pen tablet and the touch panel (which are not shown). The input section 101 includes the central processing unit (CPU) 114, the storage unit such as the memory 113 and the HDD (Hard Disk Drive) device 115, and a not shown monitor. The respective components are connected with one another via a data bus 101a.

The data input through the keyboard 111 and the like are received by the CPU 114 as the processor. The CPU 114 develops and activates the predetermined program which has been preliminarily stored in the memory 113, the HDD device 115 and the like so as to function as the image-taking condition input unit 131 as shown in FIG. 2. The CPU 114 develops and activates another program to transmit the control signal to the image-taking section 102 so as to function as a part of the image-taking control unit 132 as shown in FIG. 2.

The X-ray generation unit 1 as the X-ray generator and the X-ray detection unit 2 in the image-taking section 102 realize radiation of the X-ray to the subject 6, and detection thereof likewise the generally employed X-ray CT device. Typically, the distance between the X-ray generation point of the X-ray generation unit 1 and the X-ray input plane of the X-ray detection unit 2 is set to 1000 [mm]. Typically, the diameter of the opening 7 is set to 700 [mm], and the time period required for the single rotation of the rotary plate 4 is set to 1.0 [s]. The X-ray detection unit 2 includes a known X-ray detection element constituted by a scintillator and a photodiode. A plurality of detection elements are arranged in the channel direction, that is, the direction along the arc at an equal distance from the X-ray generation unit 1 in the plane parallel to the main surface of the rotary plate 4, and the slicing direction, that is, the body axis direction of the subject 6.

For example, the number of the X-ray detection elements (hereinafter referred to as channel number) in the channel direction is set to 1000. Typically, each size of the X-ray detection element in the channel direction is set to 1 [mm]. The image-taking frequency of the image-taking section 102 per rotation of the rotary plate 4 is set to 900. The single image-taking operation is performed for each rotation of the rotary plate 4 at 0.4°. The angle of the rotary plate 4, at which the image-taking operation is performed will be referred to as a projection angle. The respective specifications are not limited to those described above, but may be varied in accordance with the structure of the X-ray CT device.

The image generation section 103 includes a processing unit constituted by the data acquisition system (Data Acquisition System, hereinafter referred to as DAS) 119 and the central processing unit (Central Processing Unit, hereinafter referred to as CPU) 121, a storage unit such as the memory 120 and the HDD device 122, and the monitor 123. Those components are connected via a data bus 103a. The DAS 119 functions as the signal collection unit 134 as shown in FIG. 2. The CPU 121 as the processing unit is configured to function as the correction processing unit and the iterative approximation reconstruction unit 136 as shown in FIG. 2 by developing and activating the predetermined program preliminarily stored in the memory 120 and the HDD device 122. The monitor 123 functions as the image display unit 137.

The signal detected by the X-ray detection unit 2 of the image-taking section 102 is collected by the DAS 119 functioning as the signal collection unit 134, and converted into the digital signal so as to be received by the CPU 121. The CPU 121 performs the image reconstruction by correction and iterative approximation. The data are stored by the HDD device 122, and externally input/output in need. The image reconstructed CT image is displayed on the monitor 123 such as the liquid crystal display and the CRT functioning as the image display unit 137. As described above, the CPU 121, the memory 120, and the monitor 123 may be shared by the input section 101.

Figure 3:
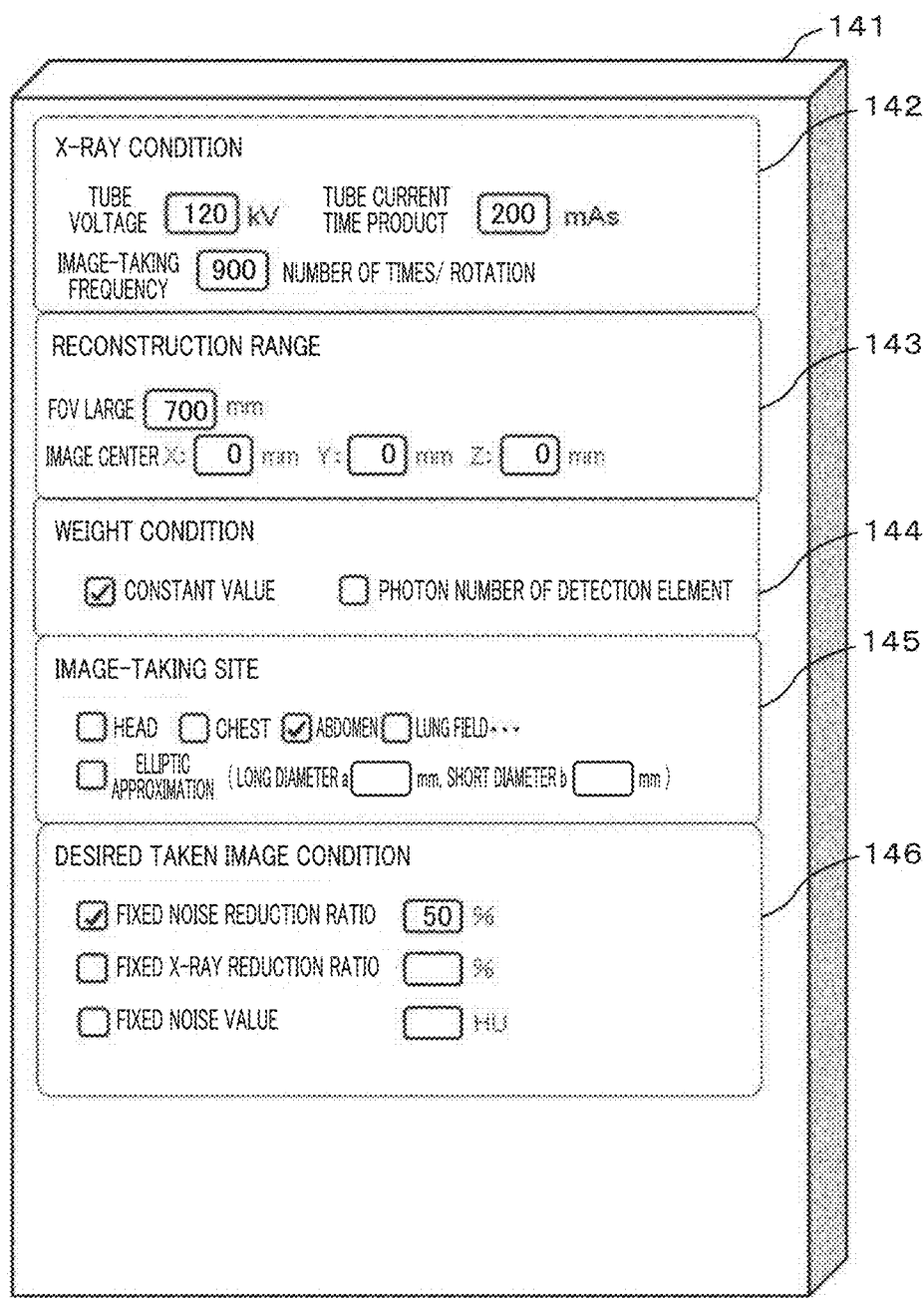
FIG. 3 is an explanatory view of an image-taking condition reception screen of the device according to the first embodiment.

The flow of image-taking operation performed by the X-ray CT device according to the first embodiment will be described with respect to the functional block diagram shown in FIG. 2 referring to the hardware structure as shown in FIG. 1 and a screen example as shown in FIG. 3. FIG. 3 is a view showing an example of an image-taking condition reception screen 141 which is displayed on the monitor 123 of the image-taking condition input unit 131.

The image-taking condition input unit 131 displays the image-taking condition reception screen 141 as shown in FIG. 3 on the monitor 123 for accepting the operator's input. The image-taking condition reception screen 141 as shown in FIG. 3 includes an X-ray condition set region 142 for setting a tube voltage corresponding to the energy and output for radiating X-ray, the tube current time product, and the image-taking frequency per rotation, a reconstruction range set region 143 for setting the reconstructed image range, a weight set region 144 for selecting the weight used for the iterative reconstruction, an image-taking site set region 145 for setting the image-taking site, and an image-taking/image-setting region 146 for selecting the desired image-taking condition or the image condition.

The operator operates the mouse 112 and the keyboard 111 while viewing the image-taking condition reception screen 141 so as to set the X-ray condition in the X-ray condition set region 142, the reconstruction range in the reconstruction range set region 143, the weight condition in the weight set region 144, the image-taking site in the image-taking site set region 145, and the desired image-taking condition or the image condition in the image-taking/image-setting region 146, respectively. The aforementioned operations will be described in detail as follows.

FIG. 3 shows an example that the operator sets the tube voltage value to 120 [kV], the tube current time product to 200 [mAs], and the image-taking frequency to 900 [times/rotation] in the X-ray condition set region 142. FIG. 3 represents the example of using the X-ray with energy spectrum of single type. In the case of a multi-energy CT using the X-ray of two or more types, such items as the tube voltage, the tube current time product, and the image-taking frequency are added to the X-ray condition set region 142 so as to perform setting for each type of the X-ray in the similar manner.

Referring to the reconstruction range set region 143 as shown in FIG. 3, the operator sets the reconstruction range (field of View, hereinafter referred to as FOV) as an image reconstruction region. The reconstruction range set region 143 as shown in FIG. 3 is designed to set the reconstruction range by setting the size and the center position of the FOV. The example of the embodiment defines the FOV as having the square shape. In this example shown in FIG. 3, each side of the FOV is set to 700 [mm], and the center position of the FOV is set to be equivalent to the rotation center, that is, X=Y=Z=0 [mm]. The FOV does not have to have the square shape, but may be arbitrarily shaped, for example, circular shape, rectangular shape, cube-like shape, and spherical shape. The structure of the embodiment may be applied to the aforementioned case.

As for the weight set region 144 shown in FIG. 3, the weight type for the iterative reconstruction to be described later is set. The weight has two types, that is, each weight of all the detection elements set as fixed value, and the value of photon number corresponding to the data detected by the detection element. In the first embodiment, the fixed value is selected as the weight used for the iterative reconstruction. In the image-taking site set region 145 as shown in FIG. 3, as the image-taking site, the X-ray radiation object (site and tissue of head, chest, lung field) is selected, or the condition of ellipsoid derived from approximation of the X-ray radiation object is designated with the numerical value. Referring to FIG. 3, the abdomen is selected.

In the image-taking/image-setting region 146 as shown in FIG. 3, the mode is selected among those for acquiring the CT image that achieves the noise reduction ratio as the fixed value, acquiring the CT image that achieves the X-ray reduction ratio as the fixed value established, and acquiring the CT image that achieves the fixed noise value. For example, in the case where the noise reduction ratio is set to 50% as shown in FIG. 3, the CT image having the initial image noise reduced by 50% is acquired by the iterative correction. Selection of the X-ray reduction ratio as the fixed value sets the mode in which the X-ray is radiated based on the desired X-ray reduction ratio so as to acquire the CT image noise equivalent to the one derived from the generally employed analytical reconstruction method. Selection of the fixed noise value sets the mode in which the CT image with the desired noise value is acquired by the iterative correction.

The image-taking condition reception screen 141 is not limited to be configured as shown in FIG. 3. Combinations of the X-ray condition, the reconstruction range, the weight set condition, the image-taking site set condition, and the image-taking/image condition which are accepted by the image-taking condition reception screen 141 are preliminarily stored in the HDD device 115 so that the combination is read by the image-taking condition input unit 131 from the HDD device 115. In this case, the operator does not have to input the X-ray condition and the like for each operation. A plurality of setting condition combinations are preliminarily stored so as to allow the operator to select the combination from them.

The image-taking section 102 as shown in FIG. 2 is configured to perform the X-ray image-taking operation in accordance with the image-taking condition accepted by the image-taking condition input unit 131. In response to the instruction to start image-taking operation by using the mouse 112 and the keyboard 111, the CPU 114 outputs the signal to the bed controller 118 and the gantry controller 116 of the image-taking control unit 132. The bed controller 118 controls the bed 5 to move in the rotary axis direction of the rotary plate 4 in response to the control signal, and stops movement of the bed 5 when the image-taking site of the subject 6 coincides with the X-ray passage range between the X-ray generation unit 1 and the X-ray detection unit 2, that is, the image-taking position. This makes it possible to complete placement of the subject at the image-taking position.

The gantry controller 116 starts rotating the rotary plate 4 via the drive motor simultaneously with the instruction to start the image-taking from the CPU 114. At a time point when the rotation speed of the rotary plate 4 is brought into the constant state, and placement of the subject 6 onto the image-taking position is finished, the CPU 114 sends the instruction to the X-ray controller 117 with respect to the X-ray radiation timing of the X-ray generation unit 1, and the image-taking timing of the X-ray detection unit 2. In response to the instructions, the X-ray controller 117 allows radiation of X-ray from the X-ray generation unit 1, and the X-ray detection unit 2 starts image-taking by detecting the X-ray. The X-ray controller 117 determines the energy spectrum and output of X-ray to be radiated in accordance with the tube voltage of the X-ray generation unit 1 and the tube current time product set by the operator.

In this embodiment, the use of the X-ray with the single type of energy spectrum has been explained. However, the structure of the embodiment is applicable to the multi-energy CT. In such a case, the control may be executed by radiating X-ray with two or more types of energy spectrum through high-speed switching of the tube voltage for each rotation, or during the single rotation so as to acquire the image-taking data.

The signal collection unit 134 of the image generation section 103 converts the output signal of the X-ray detection unit 2 into the digital signal, and stores the signal in the memory 120. The correction processing unit 135 subjects the data to correction, for example, the offset correction for calibrating zero value of the X-ray detection signal, the reference correction for correcting dispersion of the signal component detected at each projection angle, and the known air calibration process for correcting sensitivity between the detection elements for the purpose of acquiring the measured projection data of the subject 6. The measured projection data are transmitted to the iterative approximation reconstruction unit 136.

Figure 4:
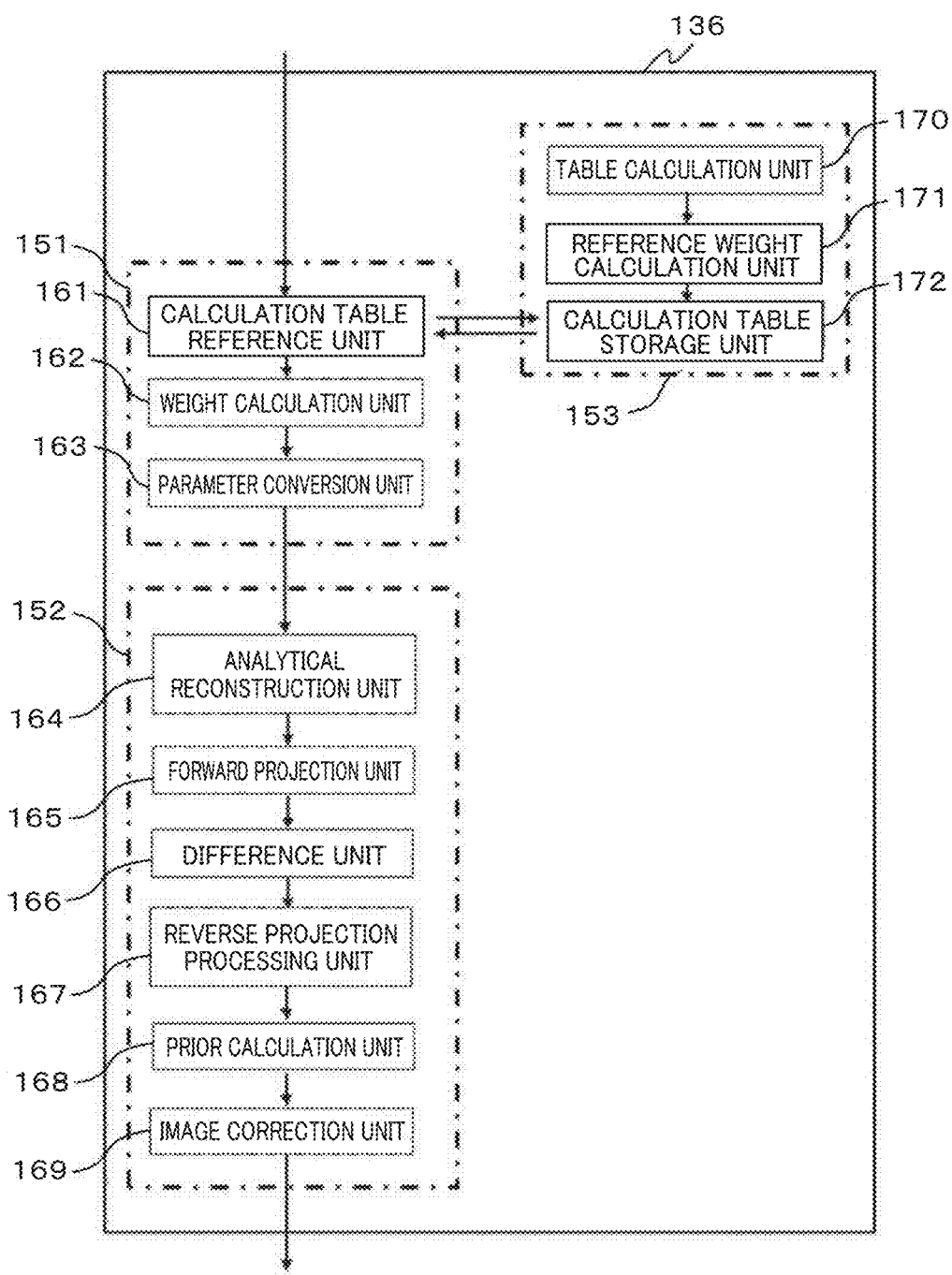
FIG. 4 is a functional block diagram explaining functions of the iterative approximation reconstruction unit according to the first embodiment.

FIG. 4 shows further detailed functional structure of the iterative approximation reconstruction unit 136 according to the embodiment. The iterative approximation reconstruction unit 136 realized by software includes a parameter determination unit 151 for determining the optimum parameter from the preliminarily calculated table based on the setting accepted by the image-taking condition reception screen 141, an iterative correction unit 152 for iteratively correcting the CT image by introducing the determined parameter, and a table unit 153 for preliminarily acquiring the calculation table.

The parameter determination unit 151 includes a calculation table reference unit 161 that refers to the reference parameter from the table unit 153 based on the accepted setting, a weight calculation unit 162 for calculating each weight of the CT image at the respective positions based on the weights of the respective detection elements, and a parameter conversion unit 163 for conversion into parameters at the respective positions by using the reference parameter and the weights at the respective positions.

The iterative correction unit 152 includes an analytical reconstruction unit 164, a forward projection unit 165, a difference unit 166, a reverse projection processing unit 167, a Prior calculation unit 168, and an image correction unit 169. The thus structured iterative correction unit 152 iteratively corrects the CT image so that the difference between the calculated projection data derived from forward projection of the CT image by calculation and the measured projection data is equalized. The Prior calculation unit 168 multiplies the value calculated from the differential value of the CT value between pixels that constitute the CT image by the iterative reconstruction parameter, and then adds the calculated result to the corrected image after Likelihood calculation. The aforementioned process allows reduction of the difference in the CT value between pixels during iterative correction, resulting in the noise reducing effect.

The table unit 153 includes a table calculation unit 170, a reference weight calculation unit 171, and a calculation table storage unit 172, which is partially formed on the storage unit. The aforementioned structure preliminarily uses the representative phantom to acquire the table having a relationship of the noise reduction ratios of the CT image in accordance with the respective parameters as reference (hereinafter referred to as reference parameter), and the weight at the reference position. In this embodiment, the ROI for measurement of noise and weight is set at the rotation center position. However, it may be set at the position around the rotation center.

In this embodiment, based on the setting accepted from the operator, the preliminarily calculated table is referred to ensure determination of the parameter in accordance with the weight at the respective positions. As a result, the iterative correction unit 152 is capable of determining the parameter after the Prior calculation at the respective positions. This makes it possible to acquire the CT image that achieves the desired noise reduction ratio irrespective of the CT image region.

Figure 5A:
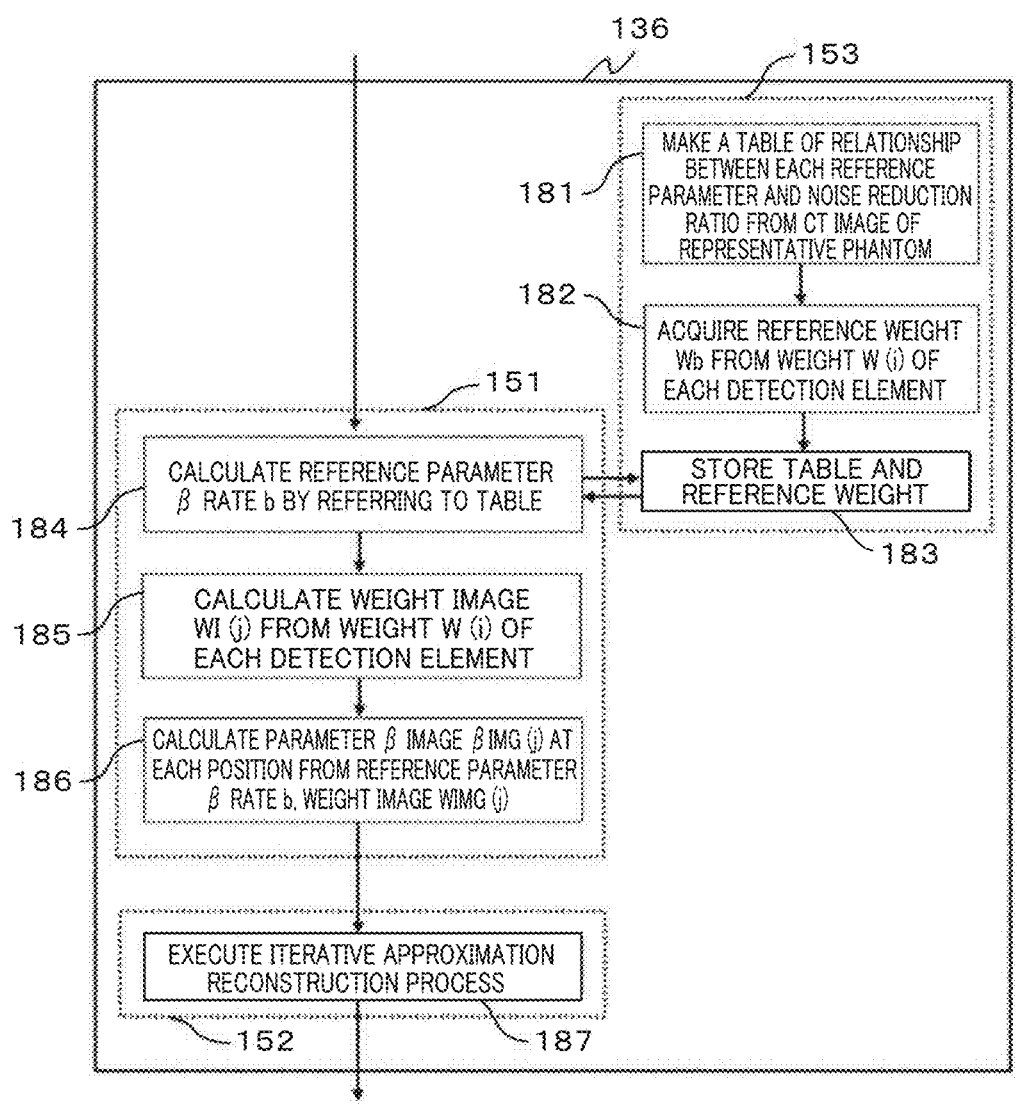
FIG. 5A is a flowchart explaining calculation procedure performed by the iterative approximation reconstruction unit according to the first embodiment.

The respective functional blocks operate as indicated by the flowchart of FIG. 5A, which will be described in detail hereinafter. The table unit 153 will be described first.

Figures 5B, 6A:
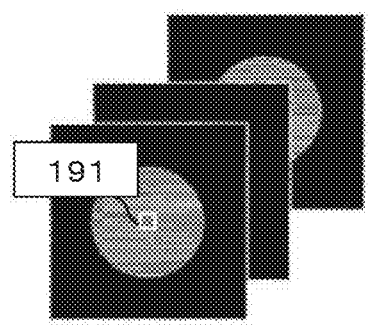
FIG. 5B represents an example of a table referred by the iterative approximation reconstruction unit according to the first embodiment.
FIG. 6A is a view of CT images explaining results of calculation performed by a table calculation unit according to the first embodiment.

In step 181 of FIG. 5A, by the use of the result preliminarily derived from iterative correction of the CT image of the representative phantom, the table calculation unit 170 makes a table of the relationship between the respective reference parameters at the reference positions, and the noise reduction ratio as indicated by FIG. 5B to be described later.

FIG. 6A shows tomographic planes of a cylindrical phantom constituted by water with diameter of 30 cm, and height of 100 cm. The noise of the ROI 191 set at the rotation center is measured from the CT image iteratively corrected by using the respective reference parameters $\beta_b$. The position of the ROI is not limited to the rotation center. It is possible to set a plurality of ROIs positioned around the area other than the rotation center. It is possible to acquire either the table corresponding to the respective ROIs, or the averaged table of measured values of the ROIs.

Figure 6B:
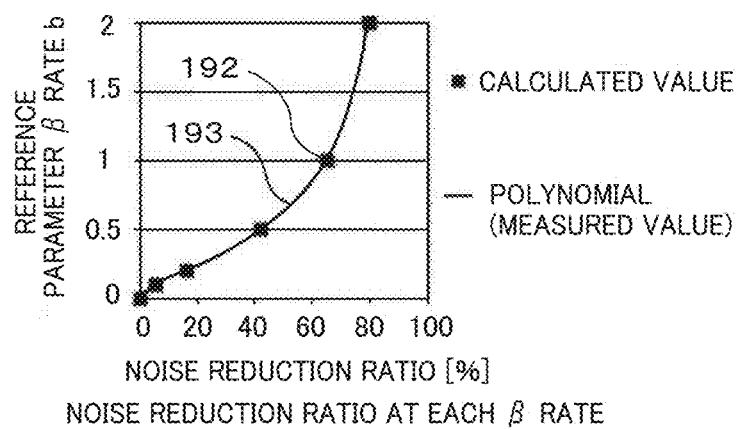
FIG. 6B represents an example of the noise reduction ratio as a result of calculation performed by the table calculation unit according to the first embodiment.

FIG. 6B shows a table of calculated relationship between the respective reference parameters $\beta_b$ and the noise reduction ratio. A plot 192 as shown in FIG. 6B denotes the measured value of noise. An approximate curve 193 is acquired from the plurality of plots 192 by using the known least squares method. This makes it possible to calculate the noise reduction ratio from any of the reference parameters $\beta_b$. Either simulation data derived from the virtual X-ray CT device or measured data derived from the actual X-ray CT device may be used for the calculated table.

Figure 7:
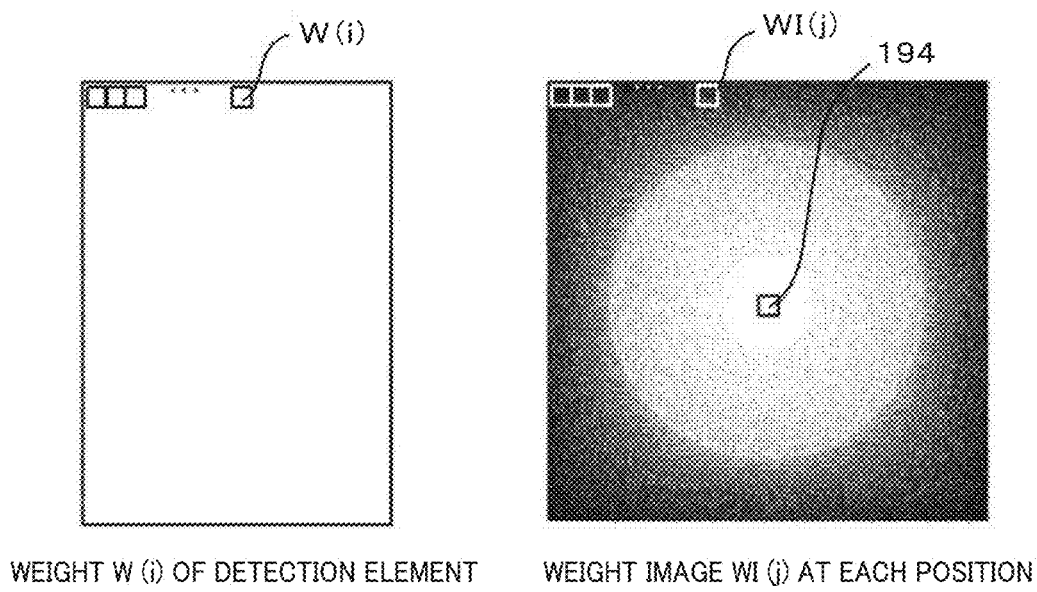
FIG. 7 is an explanatory view with respect to the result of calculation performed by a reference weight calculation unit according to the first embodiment.
Figure 8:
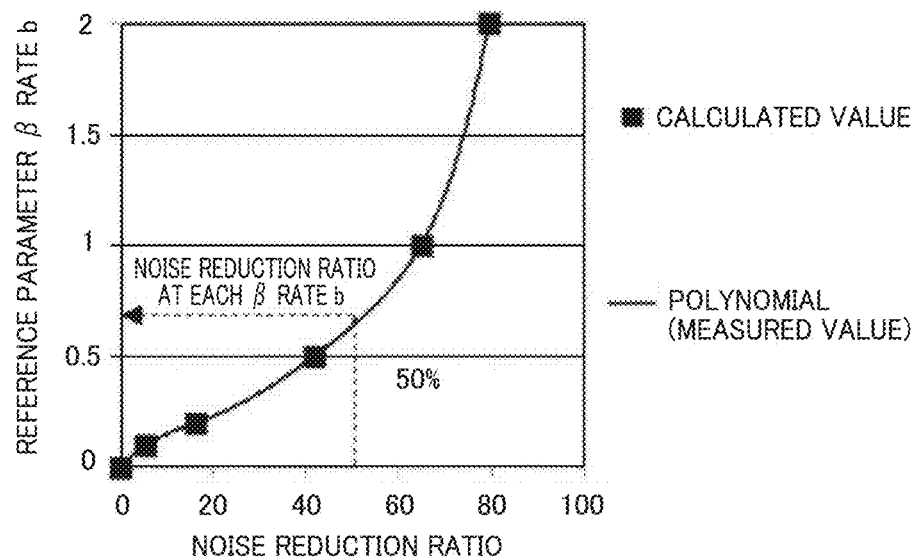
FIG. 8 is an explanatory view of the result of calculation performed by a calculation table reference unit according to the first embodiment.

In step 182 of FIG. 5A, the reference weight calculation unit 171 calculates a weight image $W_f(j)$ from the weights $W(i)$ of each detection element in accordance with the FOV and its center position designated by the operator to acquire the weight $W_b$ at the reference position (hereinafter referred to as reference weight). In the case where the FOV takes three values, that is, FOV=300, 500, 700 [mm], and the center position of the FOV has two types, that is, X=Y=Z=0 [mm], and X=30 [mm] and Y=Z=0 [mm], six types of reference weights $W_b$ in total are acquired. Preferably, the reference position is the same as that of the ROI used for noise measurement performed by the table calculation unit 170. It is possible to use a plurality of ROIs in the peripheral region at positions rather than the center. Left and right sides of FIG. 7 indicate each weight $W(i)$ of the respective detection elements, and the weight image $W_f(j)$ of the CT image at the center position of the FOV set to X=Y=Z=0 [mm]. Preferably, the table unit 153 uses the constant value for the weight $W(i)$ of the detection element. The left side of FIG. 7 indicates setting of the weight $W(i)=1$ of the detection element. The weight of the detection element is not limited to 1, but may be set to the value other than 1. The reference weight $W_b$ is obtained as a calculation result of the weight image of the ROI 194 shown in the right side of FIG. 7 by using the formula (3).

[Formula 3]

$$W_b = \sum_{i=1}^{I} W(i)C(i, j) \sum_{l=1}^{L} C(i, l) \quad (3)$$

In step 183 as shown in FIG. 5A, the calculation table storage unit 172 stores the calculated calculation table and the reference weight into the memory 120, the HDD device 122 and the like. The table unit 153 has to be executed prior to shipment of the device, or image-taking of the subject. The following process will be executed in image-taking of the subject.

Referring to FIG. 5B, the calculation table is acquired by setting the Ramp filter as the reconstruction filter used for image reconstruction while setting the update frequency to 20. In this embodiment, the image-taking conditions or reconstruction conditions are not limited to those described above. It is possible to acquire the calculation tables individually in accordance with the respective tube voltage, the bed operation speed, and other image-taking condition or reconstruction condition. For example, as FIG. 5B shows, the table unit 153 acquires the calculation table corresponding to the respective update frequencies, and the respective reconstruction filters, and stores the acquired table into the calculation table storage unit 172 as the approximation curve 193 as shown in FIG. 6B. The calculation table reference unit 161 to be described later makes reference to the suitable calculation table and the reference weight $W_b$ from the calculation table storage unit 172 based on the respective image-taking conditions or the respective reconstruction conditions.

First, the parameter determination unit 151 will be described. In step 184 of FIG. 5A, based on the condition displayed on the image-taking condition reception screen 141, the calculation table reference unit 161 calculates the reference parameter $\beta_b$ while referring to the table calculated by the table unit 153. The reference parameter $\beta_b$ is calculated based on the desired reduction ratio set to 50% in reference to the table shown in FIG. 5B.

Figure 9:
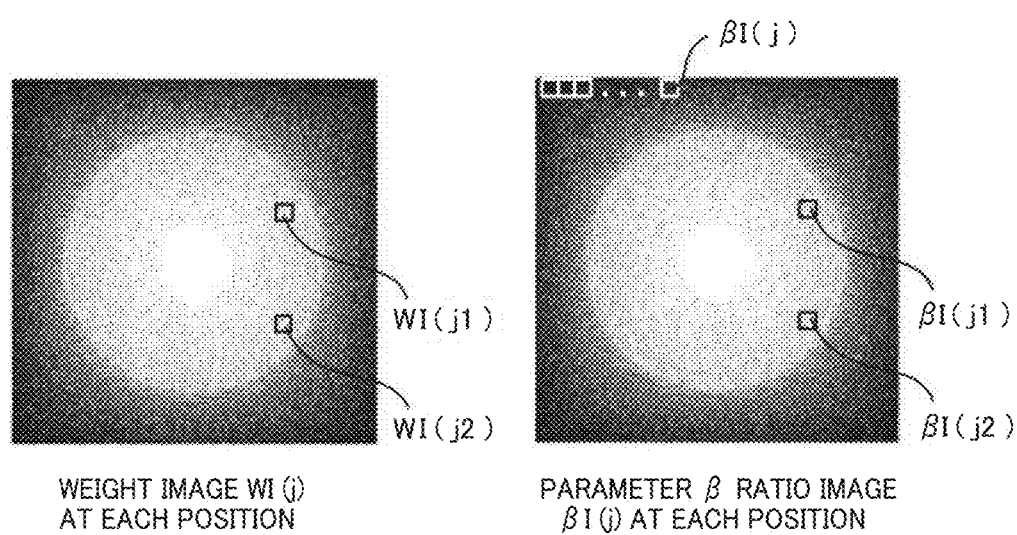
FIG. 9 is an explanatory view of the result of calculation performed by a weight calculation unit according to the first embodiment.

In step 185 of FIG. 5A, the weight calculation unit 162 calculates the weight images $W_I(j)$ from the weights $W(i)$ of the respective detection elements. The left side of FIG. 9 shows the weight images $W_I(i)$ of the CT images at the respective positions. As the formula (3) shows, each of weights $W_I(j1)$, $W_I(j2)$ at the respective positions j1, j2 has a different value.

A parameter conversion unit 175 calculates parameter β images $\beta_I(j)$ at the respective positions as expressed by the following formula (4) by using the reference weight $W_b$ acquired in the same FOV in image-taking at the center thereof, and calculated reference parameters $\beta_b$, and the calculated weight images $W_I(j)$.

[Formula 4]

$$\beta_1(j) = \beta_b \cdot \frac{W_i(j)}{W_b} \quad (4)$$

The right side of FIG. 9 shows the calculated parameter β images $\beta_I(j)$ at the respective positions. Each of the images $\beta_I(j1)$, $\beta_I(j2)$ at the respective positions j1, j2 has a different value.

In the embodiment, a plurality of calculation tables may be stored in accordance with the image-taking condition such as the tube voltage, the reconstruction condition such as the FOV, and types of the measured projection data. This makes it possible to reduce deviation of the iterative reconstruction parameter from the true value owing to the different condition.

The iterative correction unit 152 as shown in FIG. 5A will be described. In step 187 of FIG. 5A, the iterative correction unit 152 iteratively corrects the CT image by using the parameter β image $\beta_I(j)$ calculated by the parameter determination unit 151 so as to generate the CT image having noise removed with high accuracy.

The process executed in step 187 will be described in detail in reference to the flowchart of FIG. 10.

Figure 10:
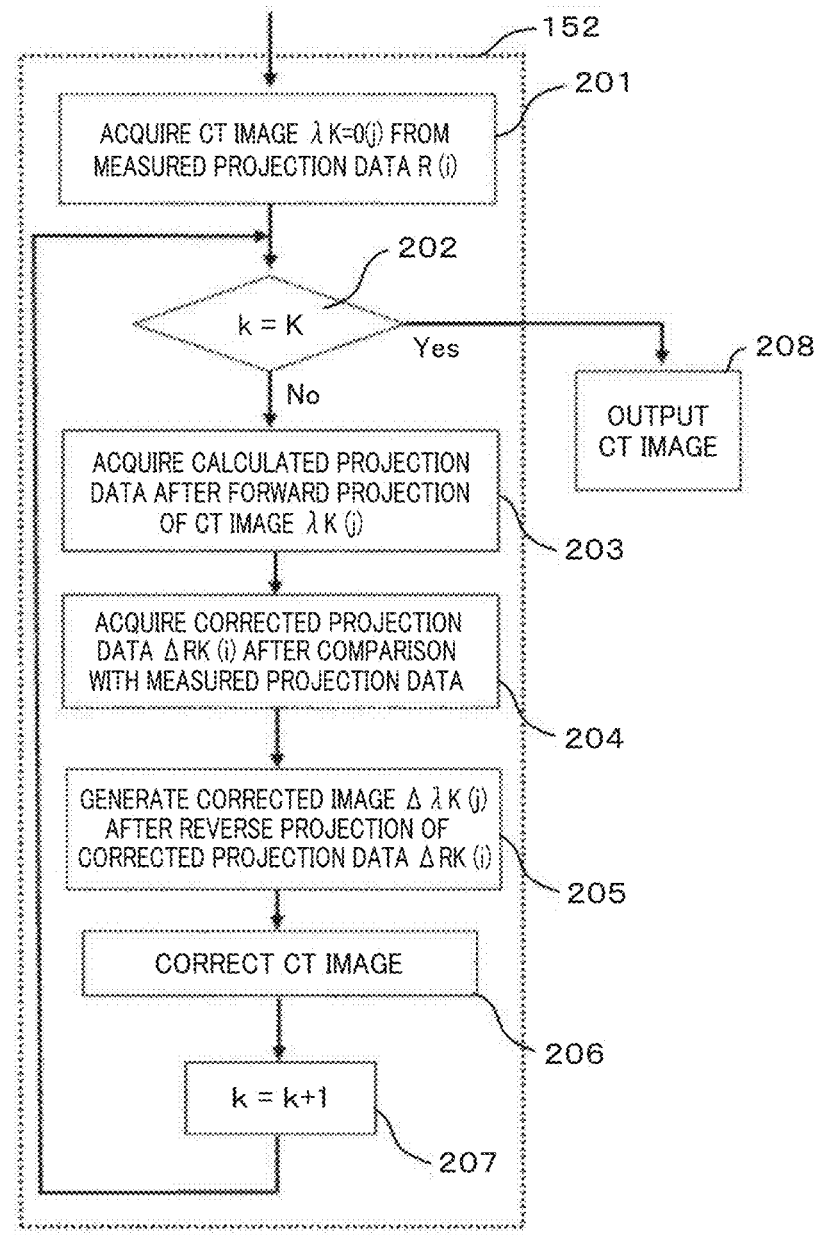
FIG. 10 is a flowchart explaining the procedure of calculation performed by an iterative correction unit according to the first embodiment.

The step 187 includes steps 201 to 208 as shown in FIG. 10. In step 201, the analytical reconstruction unit 164 of the iterative correction unit 152 shown in FIG. 4 calculates a CT image $\lambda^{k=0}$ (j) from the measured projection data R(i) corrected by the correction processing unit 135 through the analytical reconstruction method such as the known Feldkamp method.

In step 202, the CT image $\lambda^{k=0}$ (j) is used as the initial image to iteratively correct the CT image in steps 203 to 206 until the correction frequency k reaches the predetermined correction frequency K.

The known iterative approximation reconstruction method may be employed for the image correction algorithm. The embodiment will be described by taking the use of SPS (Separable-Paraboloidal-Surrogate) method as an example. The SPS is expressed by the following formula (5).

[Formula 5]

$$\lambda^{k+1}(j) = \lambda^k(j) - \frac{\sum_{i=1}^{I} W(i)C(i,j)\left(R(i) - \sum_{l=1}^{L} C(i,l)\lambda^k(l)\right) + P1}{\sum_{i=1}^{I} W(i)C(i,j)\sum_{l=1}^{L} C(i,l) + P2} \quad (5)$$

where W(i) denotes the weight indicating the image correction rate, P1, P2 denote the formulae for calculating numerator and denominator of Prior, respectively. The iterative approximation reconstruction expressed by the formula (5) will be performed in steps 203 to 206 as described below.

In step 203, the forward projection unit 165 (FIG. 4) calculates the following formula (6) to subject the pixel of the CT image $\lambda^k(j)$ to the forward projection process so as to acquire the calculated projection data.

[Formula 6]

$$\sum_{l=1}^{L} C(i,l)\lambda^k(l) \quad (6)$$

where l denotes the number of L pixels on the line for connecting the pixel j to be corrected and the X-ray detection unit i. The C(i, l) denotes the contribution rate of the pixel l to the X-ray detection unit i. Different values are set as the C(i, l) depending on the position of the X-ray detection unit, the forward projection calculation, or the reverse projection calculation method.

In step 204, the difference unit 166 as shown in FIG. 4 subtracts the calculated projection data expressed by the formula (6) from the measured projection data R(i) expressed by the following formula (7) to acquire the corrected projection data $\Delta R^k(i)$.

[Formula 7]

$$\Delta R^k(i) = R(i) - \sum_{l=1}^{L} C(i,l)\lambda^k(l) \quad (7)$$

Then in step 205, the reverse projection processing unit 167 as shown in FIG. 4 executes reverse projection process of the corrected projection data $\Delta R^k(i)$ by calculating the following formula (8) to generate the corrected image $\Delta \lambda^k$ (j).

[Formula 8]

$$\Delta\lambda^k(j) = \frac{\sum_{i=1}^{I} W(i)C(i,j)\Delta R^k(i) + P1}{\sum_{i=1}^{I} W(i)C(i,j)\sum_{l=1}^{L} C(i,l) + P2} \quad (8)$$

The values derived from the following formulae (9), (10) by the Prior calculation unit 168 shown in FIG. 4 are used as P1, P2 of the formula (8). The formulae (9), (10) are examples for calculating the P1 and P2. The P1 is obtained by calculating the first order derived function as expressed by the formula (9), and the P2 is obtained by calculating the second order derived function as expressed by the formula (10).

[Formula 9]

$$P1 = \beta \sum_{m \in N_j} d_{jm} \psi(\lambda_j^k - \lambda_m^k) \quad (9)$$

[Formula 10]

$$P2 = \beta \sum_{m \in N_j} d_{jm} \frac{\psi(\lambda_j^k - \lambda_m^k)}{\lambda_j^k - \lambda_m^k} \quad (10)$$

In the formulae (9) and (10), β denotes a fixed iterative reconstruction parameter indicating Prior intensity, and the parameter β image $β_I(j)$ at each position calculated by the parameter determination unit 151 replaces β. The term $\psi(\lambda_j^k - \lambda_m^k)$ is a function having the difference value $(\lambda_j^k - \lambda_m^k)$ of the 2-pixel CT value of the CT image $\lambda^k(j)$ as a variable.

As described above, the corrected image $\Delta\lambda^k(j)$ in the formula (8) is calculated (step 205).

Then in step 206, the image correction unit 169 calculates the following formula (11) to acquire the CT image $\lambda^{k+1}(j)$ corrected by using the corrected image $\Delta\lambda^k(j)$.

[Formula 11]

$$\lambda^{k+1}(j) = \lambda^k(j) - \Delta\lambda^k(j) \quad (11)$$

Subsequent to execution of steps 203 to 206, the correction frequency k is incremented to k+1 in step 207, and the process returns to step 202. Execution of steps 202 to 207 will be repeated until the correction frequency k after increment becomes equal to the predetermined correction frequency K. In the case where the correction frequency k reaches the predetermined correction frequency K, the correction is finished. The process then proceeds to step 208 where the CT image is output to be displayed on the monitor 123 by the image display unit 137 as shown in FIG. 2.

The CT image generated by iterative approximation reconstruction is projected to form the calculated projection data which are well coincided with the measured projection data. This makes it possible to acquire the CT image derived from imaging the measured projection data with high accuracy.

In step 208 of FIG. 10, the CT image may be transmitted to the external terminal by using the network adapter via the network, for example, local area network, telephone line, internet, and the like.

In this embodiment, execution of steps 181 to 187, and 201 to 208 allows acquisition of the CT image which achieves the desired noise reduction ratio by using the parameter β images $β_I(j)$ of the CT images at the respective positions.

In the embodiment, parameters of the CT images at the respective positions are calculated from the preliminarily calculated table for use while focusing on dependency of the noise reduction effect on the measured projection data and the set value of parameter. This makes it possible to easily introduce the optimum parameter β image $β_I(j)$ which has been determined in accordance with the desired noise reduction ratio, the image-taking condition, the reconstruction condition, and the measured projection data without largely changing the iterative approximation reconstruction processing by itself.

In the embodiment, β and $β_I(i)$ are used as the parameters. However, any parameter may be employed for the present invention limitlessly. The parameter for determining the ratio between Likelihood calculation and Prior calculation may be used for the coefficient for Likelihood calculation or the one for those two types of calculation.

The iterative approximation reconstruction method as expressed by the formula (5) is only an example. It is applicable to any other known method such as OS-SPS, OS-SPS-TV, PWLS, OS-PWLS, ASIRT, MSIRT, GRADY, CONGR, ART, SART, SART-TV, OS-SART, OS-SART-TV, ML-EM, OS-EM, FIRA, RAMLA, and DRAMA.

In the embodiment, the measured projection data acquired from a rotation by one round are used to reconstruct the CT image. However, the reconstruction may be realized as the known half reconstruction or the reconstruction using the measured projection data derived from the rotation by one round or more with no limitation to the rotation only by one round.

The embodiment has been described with respect to use of the conventional scan method for acquiring the measured projection data while having the bed 5 and the gantry 3 kept in the stationary state. It is possible to apply the present invention to the measured projection data derived from any other method, for example, the step and shoot method for executing the conventional scan while operating and stopping the bed 5 sequentially at predetermined time intervals repeatedly, or the spiral scan method for taking images while moving the bed 5.

The embodiment has been described with respect to the X-ray CT device for living body, for example. However, the structure according to the embodiment may be applied to the X-ray CT device intended to be used for the non-destructive inspection such as explosive inspection and product inspection. The embodiment has been described with respect to the known third-generation multi-slice X-ray CT device as an example. The structure of the embodiment is applicable to those known first, second, or fourth generation X-ray CT device, as well as to the known device such as the single-slice X-ray CT device, and the electron beam CT.

In the embodiment, the table calculation unit 170 and the reference weight calculation unit 171 of the table unit 153, the weight calculation unit 162, and the parameter conversion unit 163 are operated prior to operation of the iterative correction unit 152 for the purpose of reducing the calculation period. However, the table calculation unit 170, the reference weight calculation unit 171, the weight calculation unit 162, and the parameter conversion unit 163 do not necessarily have to be operated in advance. They may be operated during the image-taking process, or generation of the image in accordance with the image-taking condition or the reconstruction condition designated by the operator. For example, it is possible to add the weight calculation unit 162 and the parameter conversion unit 163 as a part of the Prior calculation unit 168. In this case, the term $W_f(j)$ of the formula (4) is equivalent to the left term in the denominator of the formula (8). Accordingly, the $\beta_f(j)$ of the formula (4) is substituted for the $\beta$ of the formula (8) so as to ensure omission of the weight calculation unit 162 and the parameter conversion unit 163. This makes it possible to reduce the computational load required for the weight calculation of the overlapped images $W_f(j)$.

Second Embodiment

The X-ray CT device according to the second embodiment will be described.

The first embodiment is configured to calculate the parameter $\beta$ image $\beta_f(j)$ by using the reference parameter $\beta_b$, reference weight $W_b$, and the weight image $W_f(j)$ at each position for setting the weight set as the constant value in the weight set region 144. For setting the photon number of the detection element by the weight set region 144, the second embodiment is configured to calculate the parameter $\beta$ image $\beta_f(j)$ by using the reference parameter $\beta_b$ calculated with the weight set as the constant value, the reference weight $W_b$, and the weight image $W_f(j)$ at each position calculated with the photon number of the detection element. The structure of the X-ray CT device according to the second embodiment will be described while focusing on the structure different from that of the X-ray CT device according to the first embodiment.

Figure 11:
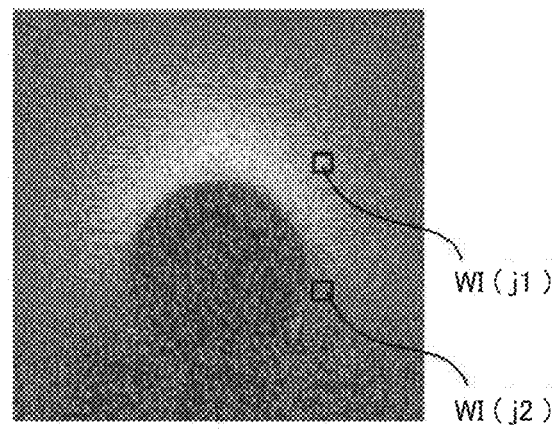
FIG. 11 is an explanatory view of the result of calculation performed by the weight calculation unit according to a second embodiment.

FIG. 11 shows the weight images $W_f(j)$ calculated from the result of taking an image of the cylindrical phantom constituted by water, having the diameter of 30 cm and height of 100 cm by using the photon number of the detection element. The phantom is moved downward from the rotation center by 10 cm. Each of the weight images $W_f(j1)$ and $W_f(j2)$ at the respective positions as shown in FIG. 11 has the different value.

The parameter conversion unit 163 calculates the parameter $\beta$ image $\beta_f(j)$ at each position expressed by the formula (4) by using the reference weight $W_b$ calculated with the weight as the constant value, the reference parameter $\beta_b$ calculated by the calculation table reference unit 161, and the aforementioned weight image $W_f(j)$. The process steps subsequent to the analytical reconstruction unit 164 are the same as those of the first embodiment. This makes it possible to acquire the CT image which achieves the desired noise reduction ratio by using the parameter $\beta$ image $\beta_f(j)$ at each position for setting the photon number of the detection element in the weight set region 144. An image of the cylindrical phantom constituted by water is taken for verifying effectiveness of the second embodiment. The phantom is moved downward from the rotation center.

Figure 12:
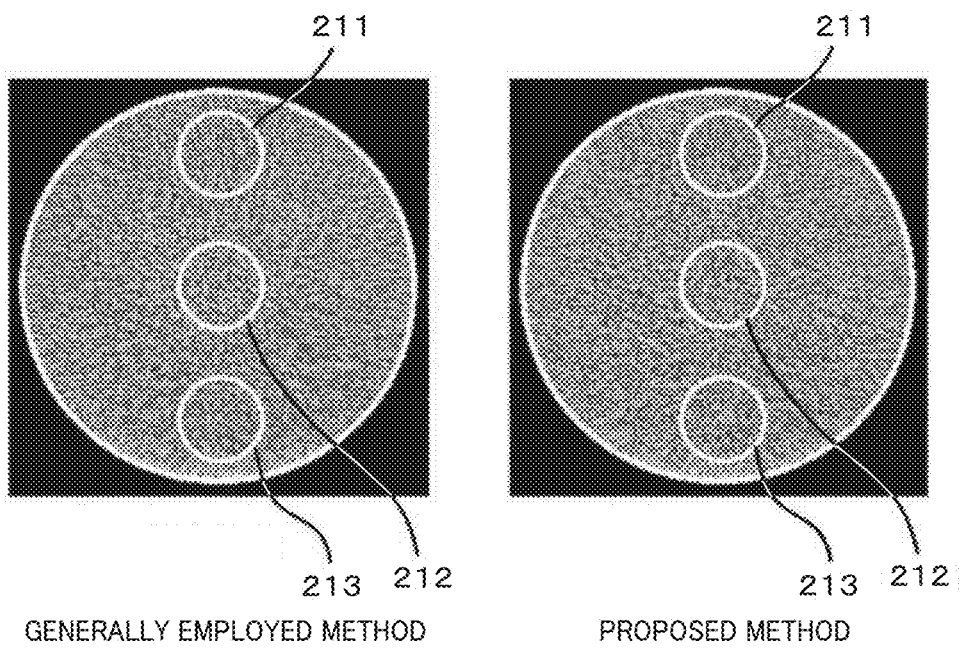
FIG. 12 is an explanatory view of CT images as a result of comparison between the generally employed method and the proposed method, and positions of ROI.

The left side of FIG. 12 shows the CT image formed by the generally employed method, which is iteratively corrected by using the parameter $\beta$ fixed at each position. The right side of FIG. 12 shows the CT image formed by the proposed method, which is iteratively corrected by using the parameter $\beta$ image $\beta_f(j)$ at each position. FIG. 12 shows the result of enlargement of the CT image. The iterative reconstruction employs the OS-SPS through the known subset method. In the weight set region 144 as shown in FIG. 3, the photon number of the detection element is set to determine the desired noise reduction ratio.

The generally employed method shown in the left side of FIG. 12 indicates excessive reduction of noise in an arrow part 211 at the lower part of the phantom compared with noise at the phantom center. Meanwhile, the proposed method shown in the right side of FIG. 12 indicates that noise at the phantom center is substantially equivalent to the one in an arrow part 212 at the lower part of the phantom.

Figure 13:
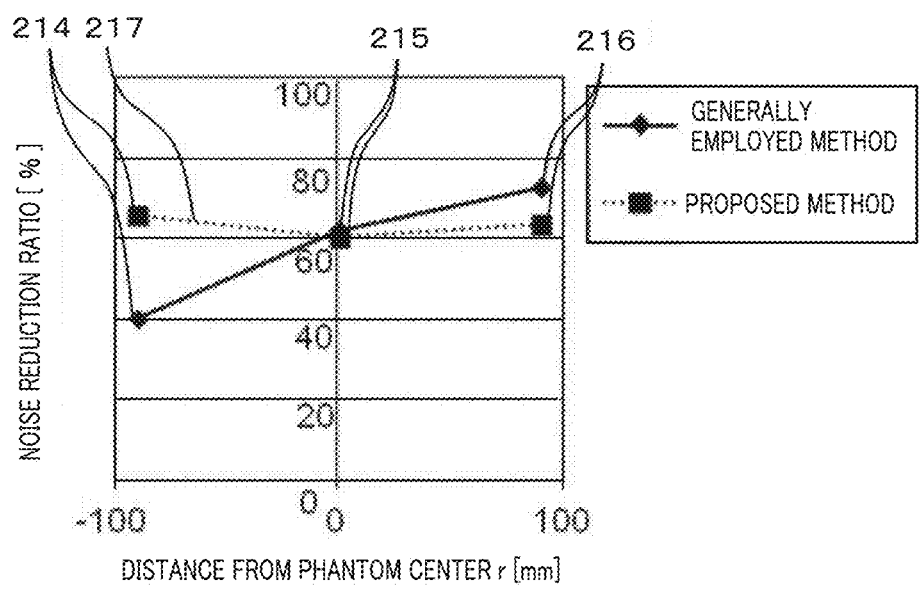
FIG. 13 is a view showing a graph representing a comparison between the generally employed method and the proposed method according to the second embodiment.

The ROI is set in each of the upper part 211, center part 212, and lower part 213 of the phantom as shown in FIG. 12 so that noise in the ROI is measured. The graph of FIG. 13 represents measurement results of noise in each ROI of the upper part 211, the center part 212, and the lower part 213 of the phantom, showing the distance from the phantom center in a horizontal axis, and noise reduction ratio in a vertical axis. A plot 214 is a measurement result of the ROI 211 at the upper part, a plot 215 is the measurement result of the ROI 212 at the center part, and a plot 216 is the measurement result of the ROI 213 at the lower part. It is assumed that the distance from the phantom center in the upward direction becomes negative, and the distance from the phantom center in the downward direction becomes positive. Compared with the generally employed method, the proposed method acquires the equal reduction ratio 217 irrespective of the distance, acquiring the result approximate to the set reduction ratio. This shows that the use of the proposed method allows acquisition of the CT image which achieves the desired noise reduction ratio.

Third Embodiment

The X-ray CT device according to the third embodiment will be described. The first embodiment is configured to calculate the parameter $\beta$ image $\beta_f(j)$ by using the reference weight $W_b$ at the rotation center set at the reference position, the reference parameter $\beta_b$, and the weight image $W_f(j)$ at each of the respective positions for setting the weight set as the constant value in the weight set region 144. The third embodiment is configured to calculate the parameter $\beta$ image $\beta_f(j)$ by using a plurality of reference weights $W_b$ in addition to the rotation center, a plurality of reference parameters $\beta_b$, and the weight images $W_f(j)$ at the respective positions. The structure of the X-ray CT device according to the third embodiment will be described while focusing on the structure different from that of the X-ray CT device according to the first embodiment.

Figure 14:
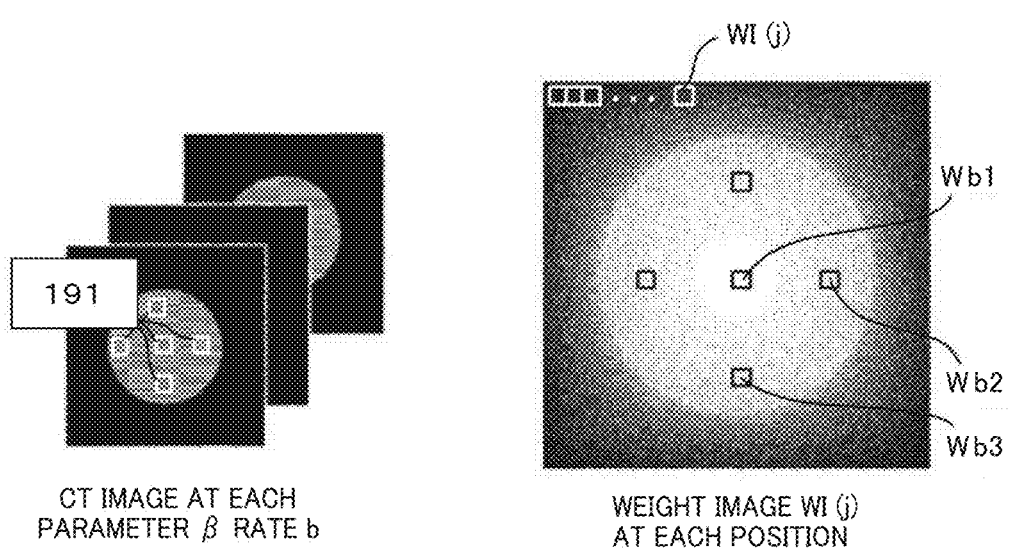
FIG. 14 is an explanatory view of results of calculation performed by the table calculation unit and the reference weight calculation unit according to a third embodiment.

The left side of FIG. 14 shows a plurality of ROIs 191 set on the CT image iteratively corrected by using the respective reference parameters $\beta_b$ in the table calculation unit 170. The ROIs 191 are set not only at the rotation center but also at the upper, lower, left and right sides each apart from the center by the distance r (=200 mm). The calculation table is acquired for each of the ROIs 191 by using the measurement results of noise in the ROIs 191 on the CT image. In this case, the reference parameters $\beta_b$ calculated in the ROIs 191 are expressed as $\beta_{b1}$, $\beta_{b2}$, $\beta_{b3}$, and the like.

The right side of FIG. 14 shows a plurality of ROIs set on the weight image $W_f(j)$ calculated from the weight set as the constant value in the reference weight calculation unit 171 for measuring the reference weight. The measured reference weights are expressed as $W_{b1}$, $W_{b2}$, $W_{b3}$, and the like. Preferably, the region in which the reference weight is measured is at the same position as the ROI 191 where noise is measured as described above. The table unit 153 has to be executed prior to shipment of the device, or image-taking of the subject. The following processes will be executed in image-taking of the subject.

The calculation table reference unit 161 as shown in FIG. 4 calculates the reference parameter $\beta_b$ from the table calculated by the table unit 153 based on the condition of the image-taking condition reception screen 141 in step 184 of FIG. 5A. For example, in the case where the noise reduction ratio is 50%, the reference parameter $\beta_b$ is calculated from the calculation table as shown in FIG. 5B. In the embodiment, the reference parameters $\beta_{b1}$, $\beta_{b2}$, $\beta_{b3}$ and the like in the plurality of ROIs 191 are acquired as shown in the left side of FIG. 14. As a result of calculation of the distance between each position of the CT image and the ROIs 191, the reference parameter $\beta_b$ with the shortest distance is selected. In this case, the known Euclidean distance between each position and the reference position is used as the distance. Then based on calculation results of the distance between each position of the CT image and the ROIs 191, the parameter conversion unit 163 selects the reference weight $W_b$ with the shortest distance.

Conventionally, at the position apart from the reference position, there may be the case of causing the problem of deteriorating accuracy for estimating the desired noise reduction ratio. This embodiment ensures to use the table with the short distance from the position compared with the generally employed case, thus improving accuracy for estimating the noise reduction ratio.

Fourth Embodiment

The X-ray CT device according to the fourth embodiment will be described. The first embodiment is configured to acquire the CT image that achieves the uniform noise reduction ratio at the respective positions in the mode for acquiring the CT image which achieves the fixed noise reduction ratio in the desired condition set region 146 as shown in FIG. 3. The fourth embodiment is configured to calculate parameter $\beta$ images $\beta_f(j)$ at the respective positions by using a noise value of the initial image, and the reference parameter $\beta_b$ determined in accordance with the noise value in the mode for acquiring the CT image having the fixed noise value in the desired condition set region 146 as shown in FIG. 3. The X-ray CT device according to the fourth embodiment will be described with respect to the structure different from that of the X-ray CT device according to the first embodiment.

Figure 15:
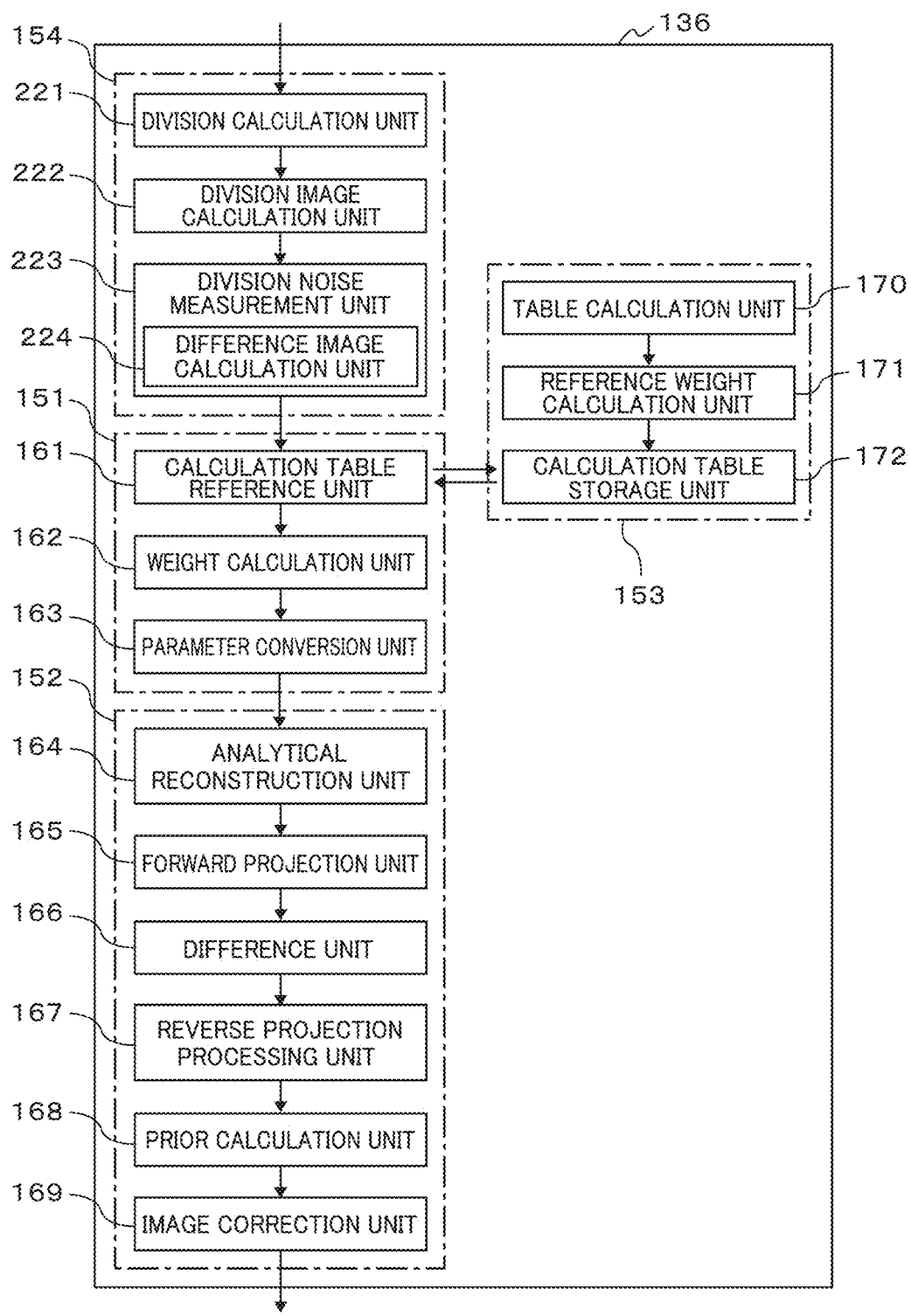
FIG. 15 is a functional block diagram explaining functions of the iterative approximation reconstruction unit according to a fourth embodiment.
Figure 16A:
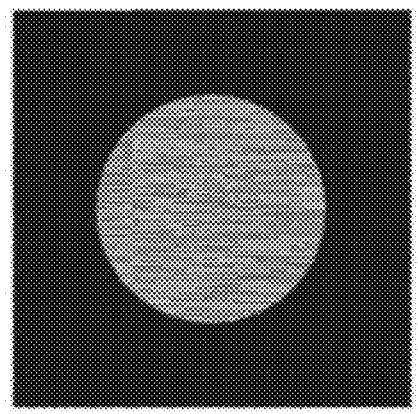
FIG. 16A is a view showing an example of the CT image for explaining results of calculation performed by a noise measurement unit and a parameter determination unit according to the fourth embodiment.
Figure 16B:
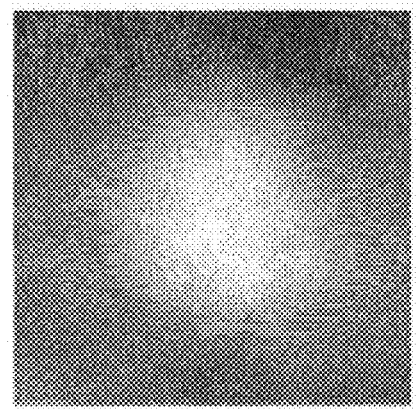
FIG. 16B is a view showing an example of an SD image for explaining results of calculation performed by the noise measurement unit and the parameter determination unit according to the fourth embodiment.

FIG. 15 is a view of the structure formed by adding the noise measurement unit 154 to the structure shown in FIG. 4. The noise measurement unit 154 calculates an SD image $N_c(j)$ indicating each noise value of the initial image at the respective positions. Detailed explanation of the noise measurement unit 154 will be made later. FIG. 16A shows the CT image calculated by the analytical reconstruction unit 164. FIG. 16B shows the SD image $N_c(j)$ of the aforementioned CT image at each of the respective positions. Then a calculation table reference unit 173 calculates an image $N_f(j)$ with the noise reduction ratio as expressed by the formula (12) by using the acquired SD images $N_c(j)$. The fixed SD as expressed by the formula (12) denotes the fixed noise value set in the desired condition set region 146 as shown in FIG. 3.

[Formula 12]

$$N_f(j)=(N_c(j)-\text{fixed SD})/N_c(j) \cdot 100 \quad (12)$$

Figure 16C:
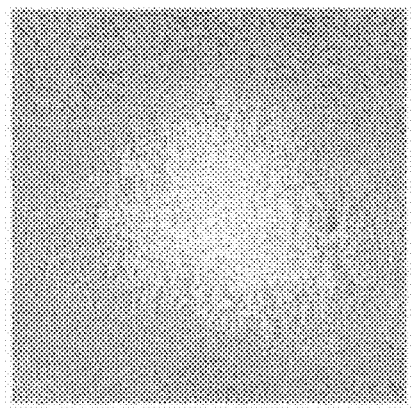
FIG. 16C is a view showing an example of an image indicating the noise reduction ratio for explaining results of calculation performed by the noise measurement unit and the parameter determination unit according to the fourth embodiment.

FIG. 16C shows the image $N_f(j)$ with the calculated noise reduction ratio. The reference parameters $\beta_{b1}(j)$ at the respective positions are calculated by using the image $N_f(j)$ with the noise reduction ratio, and the table referred by the table unit 153. The parameter conversion unit 163 calculates the parameter $\beta$ image $\beta_f(j)$ by using the following formula (13).

[Formula 13]

$$\beta_l(j) = \beta_{bl}(j) \cdot \frac{W_l(j)}{W} \quad (13)$$

Figure 16D:
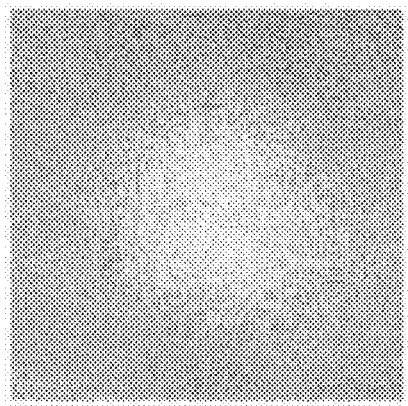
FIG. 16D is a view showing an example of a parameter $\beta$ image for explaining results of calculation performed by the noise measurement unit and the parameter determination unit according to the fourth embodiment.

FIG. 16D shows the calculated parameter $\beta$ image $\beta_f(j)$. This makes it possible to acquire the CT image with the desired noise value by using the parameter $\beta$ image $\beta_f(j)$ for acquiring the fixed noise value.

The noise measurement unit 154 as shown in FIG. 15 will be described.

Figure 17:
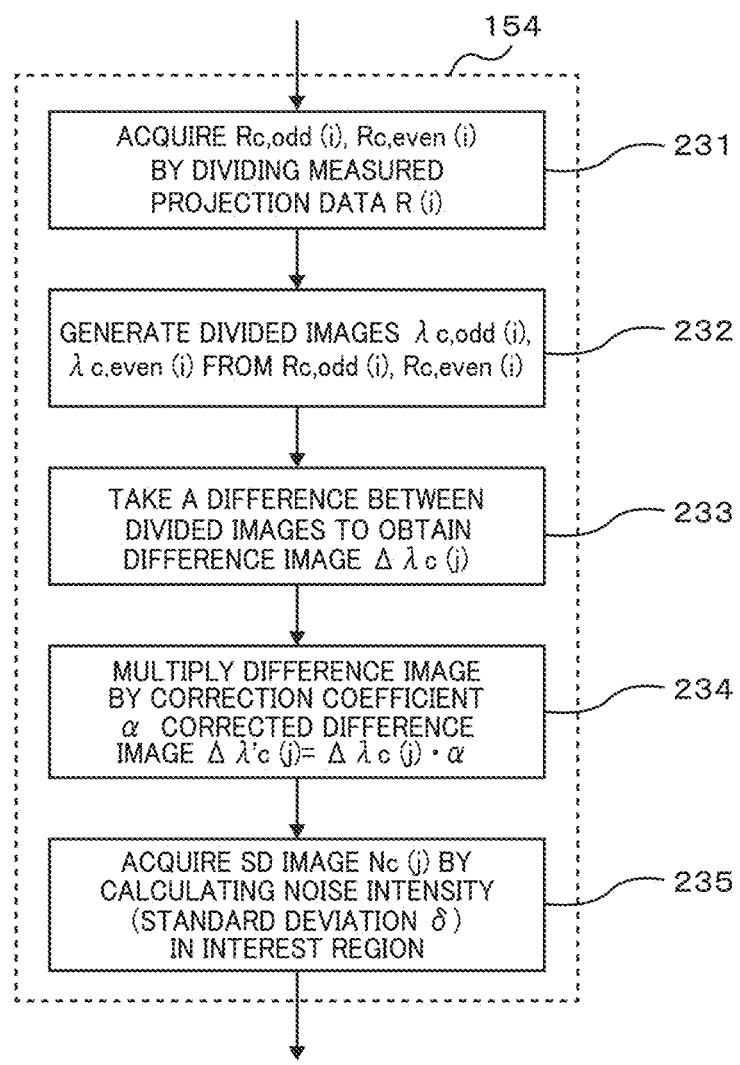
FIG. 17 is a flowchart explaining the procedure of calculation performed by the noise measurement unit according to the fourth embodiment.

In step 231 of FIG. 17, the division calculation unit 221 as shown in FIG. 15 divides the measured projection data $R(i)$ into two or more data in the channel direction. In the embodiment, the data are divided into two groups, that is, a group of measured projection data $R_{c,odd}(i)$ with odd number of the detection element, and a group of measured projection data $R_{c,even}(i)$ with even number of the detection element. The term "i" denotes the number of the detection element of the X-ray detection unit 2.

FIG. 18A shows an example of the measured projection data $R(i)$ with 1000 channels, showing a channel number in a horizontal axis, and a projection angle (rotation angles of the X-ray generation unit 1 and the X-ray detection unit 2) in a vertical axis. Each density of the measured projection data as shown in FIG. 18A indicates the corresponding pixel value (CT value).

The left side of FIG. 18B shows the measured projection data $R_{c,odd}(i)$ with odd numbers after division, and the right side of FIG. 18B shows the measured projection data $R_{c,even}(i)$ with even numbers. Both data shown in FIG. 18B are derived from dividing the measured projection data $R(i)$ shown in FIG. 18A into two groups in the channel direction, each of which has 500 channels, respectively.

In step 231, interpolation of the data between channels of the measured projection data $R_{c,odd}(i)$ and $R_{c,even}(i)$ after division allows increase in the number of channels of the measured projection data before division. For example, the data with deficient channel are calculated from values of the measured projection data between adjacent channels after division by using the known interpolation method. The linear interpolation such as arithmetic mean, or the non-linear interpolation such as spline interpolation may be used as the interpolation method. Alternatively, it is possible to use the data near the deficient channel directly as the value of the deficient channel. In the case of the aforementioned interpolation process, each number of channels of the measured projection data $R_{c,odd}(i)$ and $R_{c,even}(i)$ after division will be increased from 500 to 1000, respectively.

In step 232 of FIG. 17, a division image calculation unit 222 of CT value of the subject by executing the analytical reconstruction process from the measured projection data $R_{c,odd}(i)$ with odd numbers and $R_{c,even}(i)$ with even numbers. The term "j" denotes the pixel number of the CT image. The CT image is assumed to be constituted by J pixels. As the analytical reconstruction process, the known process, for example, Feldkamp method may be used. It is possible to acquire not only the general two-dimensional tomographic image (x, y directions) but also one-dimensional data (x direction), three-dimensional data (x, y, z directions) formed by laminating images in the body axis direction z, or four-dimensional data (x, y, z, t) in consideration of adding the time direction t to the three-dimensional data as the CT image. The left and right sides of FIG. 18C show the CT image $\lambda_{c,odd}$(j) with odd numbers, and the CT image $\lambda_{c,even}$(j) with even numbers, respectively.

In step 233 of FIG. 17, the difference image calculation unit 224 of the division noise measurement unit 223 as shown in FIG. 15 takes a difference between the CT image $\lambda_{c,odd}$(j) with odd number and the CT image $\lambda_{c,even}$(i) with even number as expressed by a formula (14) to acquire the difference image $\Delta\lambda_c$(j).

[Formula 14]

$$\Delta\lambda_c(j)=\lambda_{c,odd}(j)-\lambda_{c,even}(j) \text{ or } \Delta\lambda_c(j)=\lambda_{c,even}(j)-\lambda_{c,odd}(j) \quad (107)$$

The left side of FIG. 18D shows an example of the difference image $\Delta\lambda_c$(j). The CT images $\lambda_{c,odd}$(j) with odd number and $\lambda_{c,even}$(j) with even number are derived from reconstruction of two groups of data formed by dividing the measured projection data. Therefore, each of those images contains the same subject image. The difference image $\Delta\lambda_c$(j) has the subject image eliminated as indicated by the left side of FIG. 18D by taking the difference between both images, resulting in a distribution image of the CT value of noise contained in the CT image.

The CT value of noise expressed by the difference image $\Delta\lambda_c$(j) corresponds to the measured projection data after division. Specifically, the noise CT value is amplified by $\sqrt{2}$ times through division of the measured projection data into two groups. The value is corrected in the subsequent step 174 to acquire the corrected difference image $\Delta\lambda'_c$(j) indicating the intensity distribution of the noise CT value corresponding to the CT value of the undivided measured projection data.

Specifically, in step 234 of FIG. 17, the difference image $\Delta\lambda_c$(j) is multiplied by a correction coefficient $\alpha$ for correcting intensity of the noise CT value of the difference image $\Delta\lambda_c$(j) so as to acquire the corrected difference image $\Delta\lambda'_c$(j) as shown in the right side of FIG. 18D. In the case of dividing the data into two groups, the value is amplified by $\sqrt{2}$ times by the difference process as expressed by the formula (14). Therefore, the correction coefficient of $\alpha=1/\sqrt{2}$ is set. The corrected difference image $\Delta\lambda'_c$ denotes the information (CT value) of only noise derived from eliminating the subject information from the CT image which has been reconstructed from the undivided measured projection data.

In the case where steps 232 and 233 are executed after interpolation between channels of the measured projection data $R_{c,odd}$(i) and $R_{c,even}$(i) after division to increase the channel number to the one before division, the correction coefficient of $\alpha=1$ is set.

In step 235 of FIG. 17, the division noise measurement unit 223 sets the interest region on the corrected difference image $\Delta\lambda'_c$(j) to calculate the amplitude (intensity) of the noise CT value in the interest region. Specifically, the interest region is set at the predetermined position of the corrected difference image $\Delta\lambda'_c$. Then dispersion (amplitude) of the noise CT value in the interest region is obtained for the purpose of acquiring intensity of noise in the interest region. In this case, the standard deviation $\sigma$ is calculated as the value of dispersion. This makes it possible to acquire the noise intensity (standard deviation $\sigma$) in the interest region. The interest region is set in the range of 100 pixels in vertical direction (x-axis)×100 pixels in horizontal direction (y-axis), having the pixel j' as the center, for example.

Figure 18E:
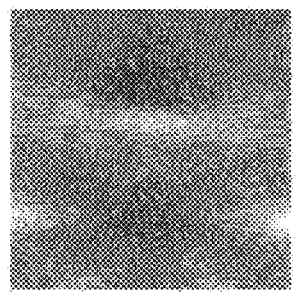
FIG. 18E is a view showing an example of the SD image for explaining results of calculation performed by the noise measurement unit according to the fourth embodiment.

The division noise measurement unit 223 calculates the noise intensity (standard deviation $\sigma$) in the interest region at the respective positions while slightly shifting the position of the center pixel j' in the interest region. The calculated value of the standard deviation $\sigma$ is made to correspond to the specific position in the interest region (for example, center pixel j') so as to generate the SD image $N_c$(j) as shown in FIG. 18E. This makes it possible to accurately calculate the SD image $N_c$(j) without being influenced by the subject, thus ensuring calculation of the noise reduction ratio images $N_f$(j) at the respective positions.

Fifth Embodiment

The X-ray CT device according to the fifth embodiment will be described. The first embodiment is configured to determine the parameter $\beta$ images $\beta_f$(j) at the respective positions by using the table calculated from the CT image of the cylindrical phantom as the representative model. The fifth embodiment is configured to calculate the parameter $\beta$ image $\beta_f$(j) by selecting the optimum table from the plurality of tables calculated by the table unit 153 in accordance with the image-taking site set in the image-taking site set region 145 as shown in FIG. 3, or the approximate elliptic information. The X-ray CT device according to the fifth embodiment will be described while focusing on the structure different from that of the X-ray CT device according to the first embodiment.

Figure 19A:
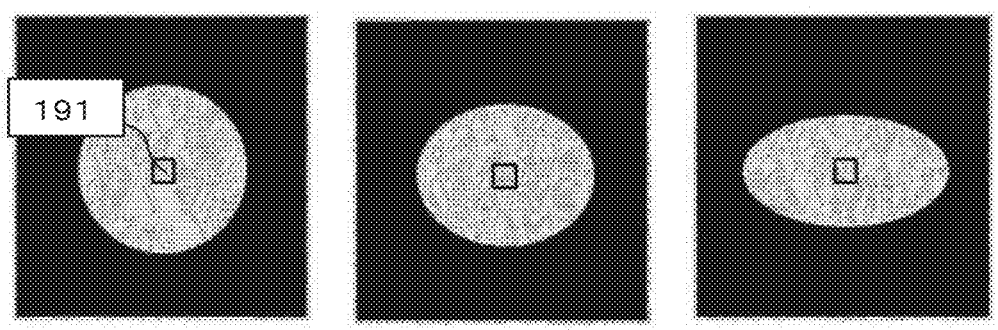
FIG. 19A is a view showing examples of the CT images each with different oblateness for explaining results of calculation performed by the table calculation unit according to a fifth embodiment.

The table calculation unit 170 as shown in FIG. 4 takes images of a plurality of elliptical phantoms each with different oblateness as representative models, and measures noise by using the CT image iteratively corrected with the respective reference parameter $\beta_b$. FIG. 19A shows CT images derived from reconstruction of three types of elliptical phantoms each with different oblateness, and the corresponding ROIs 191.

Figure 19B:
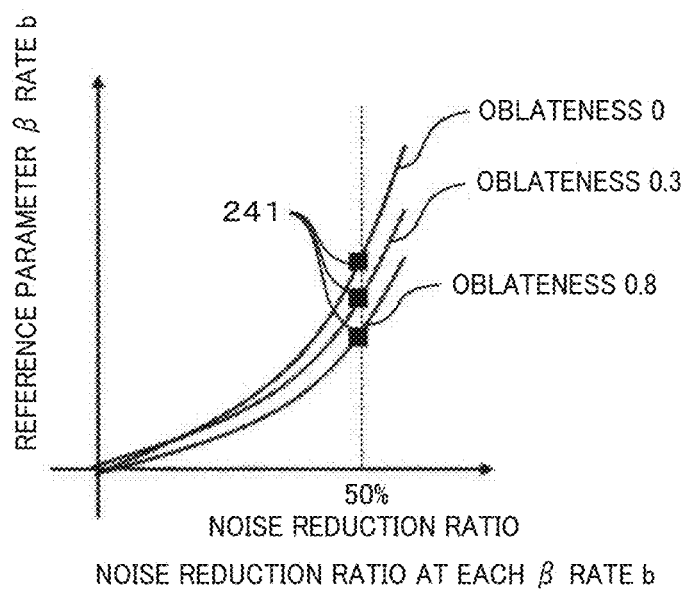
FIG. 19B is a view showing the noise reduction ratio and a reference parameter $\beta_b$ as a result of calculation performed by the table calculation unit according to the fifth embodiment.

FIG. 19B shows a table calculated by using the noise measured from the CT images of the respective elliptical phantoms, and the respective reference parameters $\beta_b$. The table varies in accordance with the oblateness of the elliptical phantom. This embodiment uses the elliptical phantoms each with different oblateness. However, it is also possible to use clinical data of such site as chest and abdomen for acquiring the calculation table.

FIG. 19B shows the case where three types of elliptical phantoms are used. As the oblateness differs from the aforementioned phantoms, there may be the case of causing the problem of deteriorating accuracy for estimating the desired noise reduction ratio. It is possible to calculate the table of the phantom with arbitrary oblateness from the table of the plurality of phantoms by using the approximation curve calculated with the known least squares method.

Figure 19C:
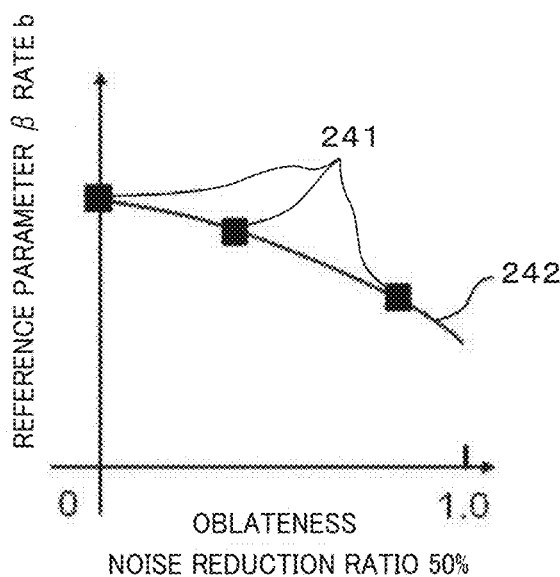
FIG. 19C is a view showing the oblateness and the reference parameter $\beta_b$ as a result of calculation performed by the table calculation unit according to the fifth embodiment.

As FIG. 19B shows, the table of relationship between the oblateness and the reference parameter $\beta_b$ is calculated by using plots 241 of the respective reference parameters $\beta_b$ with the noise reduction ratio set to 50%. The plot 241 shown in FIG. 19C indicates the measured noise value, and acquires an approximation curve 242 from the plurality of plots 241 by using the known least squares method. This makes it possible to calculate the reference parameter $\beta_b$ and the noise reduction ratio from the arbitrary oblateness. This may ensure the use of the optimum table in accordance with the image-taking site set in the image-taking site set region 145 as shown in FIG. 3, or the ellipse with arbitrary oblateness. It is therefore possible to improve accuracy for estimating the noise reduction ratio.

Figure 20:
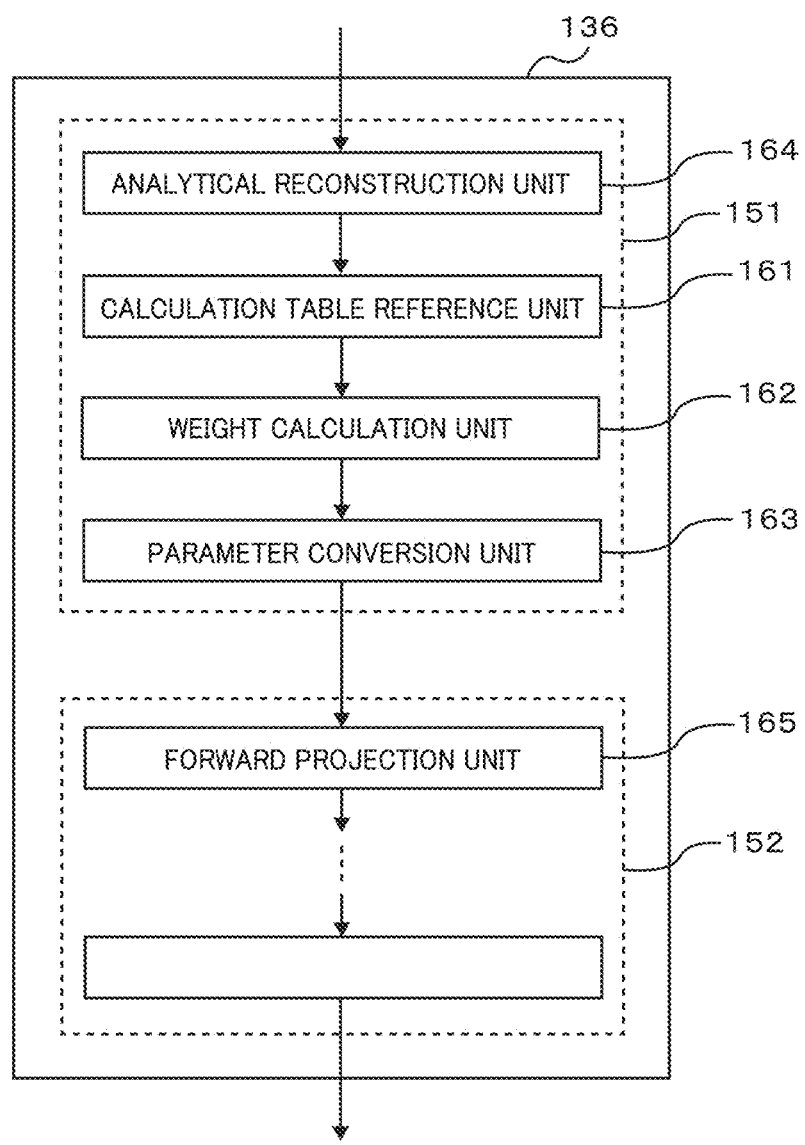
FIG. 20 is a functional block diagram explaining functions of the iterative approximation reconstruction unit according to the fifth embodiment.

The following is the description with respect to the method according to the embodiment for acquiring the CT image that achieves the desired noise reduction ratio by selecting the optimum table from the initial image. FIG. 20 is a view formed by partially changing the structure as shown in FIG. 4. Referring to FIG. 20, the arrangement order of the analytical reconstruction unit 164 is changed to the order forward of the calculation table reference unit 161.

Figure 21:
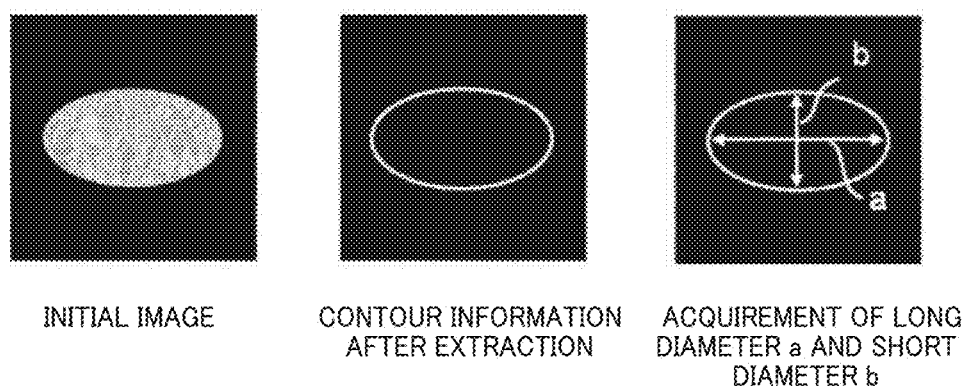
FIG. 21 is an explanatory view representing the procedure of calculation performed by the parameter determination unit according to the fifth embodiment.

As the left side of FIG. 21 shows, the initial image is calculated by using the known analytical reconstruction method. Then as the center of FIG. 21 shows, the subject contour, or the structure information is extracted from the initial image. As the right side of FIG. 21 shows, the long diameter a and the short diameter b are measured from the extracted contour or the structure information to ensure acquisition of the oblateness. The oblateness acquired from the initial image allows determination of the reference parameter $\beta_b$ by selecting the optimum table from the plurality of tables.

Sixth Embodiment

The X-ray CT device according to the sixth embodiment will be described. The fifth embodiment is configured to acquire the CT image that achieves the desired noise reduction ratio by selecting the optimum table from the initial image. The sixth embodiment is configured to acquire the CT image that achieves the desired noise reduction ratio by selecting the optimum table by using all the projection data information relating to the CT images at the respective positions. The structure of the X-ray CT device according to the sixth embodiment will be described while focusing on the structure different from that of the X-ray CT device according to the fifth embodiment.

Figure 22A:
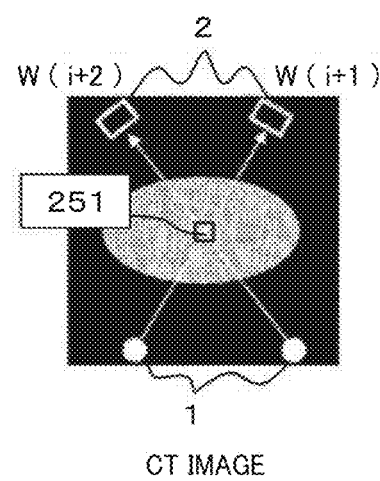
FIG. 22A is a view showing the CT image for explaining the procedure of calculation performed by the parameter determination unit according to a sixth embodiment.
Figure 22B:
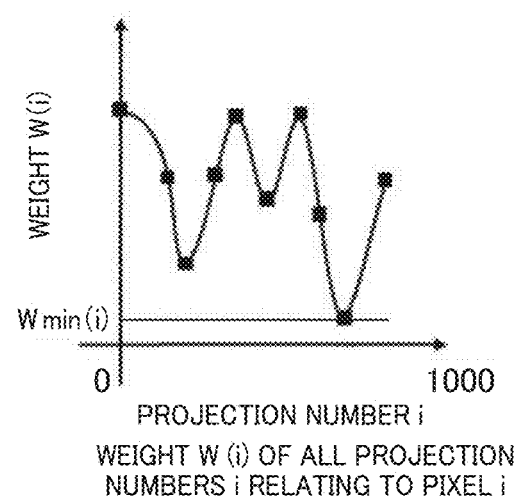
FIG. 22B is a view representing a relationship between a projection number and a weight for explaining the procedure of calculation performed by the parameter determination unit according to the sixth embodiment.

FIG. 22A shows the CT image calculated by the analytical reconstruction unit 164, and the pixel j at the center position 251. The weight W(i) is calculated from the measured projection data on the path of the X-ray source 1 and the sensor 2 which pass through the pixel j. FIG. 22B shows the weight W(i) of all projection data with the numbers i relating to the pixel j. As the photon number to be detected after transmission varies in accordance with the X-ray irradiation, subject shape and the structure shape, different weights W(i) are acquired.

Figure 22C:
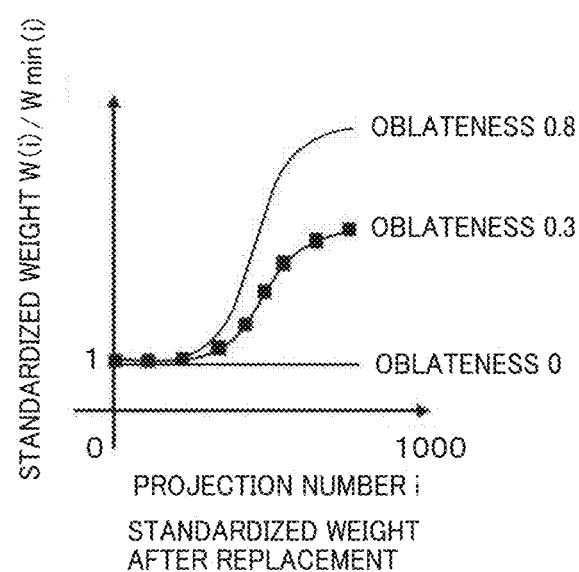
FIG. 22C is a view representing a relationship between the projection number and a standardized weight for explaining the procedure of calculation performed by the parameter determination unit according to the sixth embodiment.
Figure 22D:
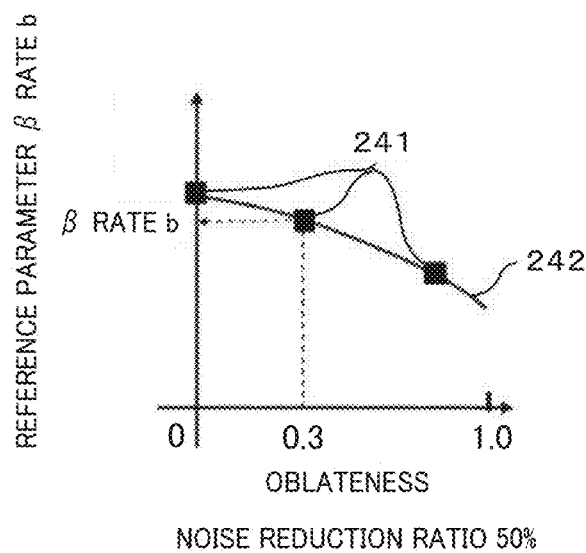
FIG. 22D is a view representing a relationship between the oblateness and the reference parameter $\beta_b$ for explaining the procedure of calculation performed by the parameter determination unit according to the sixth embodiment.

As FIG. 22C shows, the projection data are rearranged in the order from smaller value to larger value of the weight W(i). In this case, all the weights W(i) shown in FIG. 22B are standardized with the minimum value $W_{min}(i)$. FIG. 22C shows acquisition of oblateness of 0.3 by fitting with the known elliptic function. FIG. 22D shows acquirement of the reference parameter $\beta_b$ by using the acquired oblateness, and the table with noise reduction ratio set to 50%. In this embodiment, the optimum table is selected by using all the projection data information relating to the CT images at the respective positions.

The present invention is not limited to the embodiments as described above, but includes various modifications. For example, the embodiments are described in detail for readily understanding of the present invention which is not necessarily limited to the one equipped with all structures as described above. It is possible to replace a part of the structure of one embodiment with the structure of another embodiment. The one embodiment may be provided with an additional structure of another embodiment. It is further possible to add, remove, and replace the other structure to, from and with a part of the structure of the respective embodiments.

In the embodiments, the program is generated to partially or totally realize structures, functions, and processing units as described above. However, they may be partially or totally designed with the integrated circuit so as to be realized by the hardware.

LIST OF REFERENCE SIGNS

1: X-ray generation unit
2: X-ray detection unit
3: gantry
4: rotary plate
5: bed
6: subject
7: circular opening
116: gantry controller
117: X-ray controller
118: bed controller
101: input section
102: image-taking section
103: image generation section
111: keyboard
112: mouse
113: memory
114: central processing unit
115: HDD device
119: DAS
120: memory
121: central processing unit
122: HDD device
123: monitor
131: image-taking condition input unit
132: image-taking control unit
133: image-taking unit
134: signal collection unit
135: correction processing unit
136: iterative approximation reconstruction unit
137: image display unit
141: image-taking condition reception screen
142: X-ray condition set region
143: reconstruction range set region
144: weight set region
145: image-taking site set region
146: image-taking/image-setting region
151: parameter determination unit
152: iterative correction unit
153: table unit
154: noise measurement unit
161: calculation table reference unit
162: weight calculation unit
163: parameter conversion unit
164: analytical reconstruction unit
165: forward projection unit
166: difference unit
167: reverse projection processing unit
168: Prior calculation unit
169: image correction unit
170: table calculation unit
171: reference weight calculation unit
172: calculation table storage unit
191: ROI on CT image (square)
194: ROI on weight image $W_j(j)$ (square)
221: division calculation unit
222: division image calculation unit
223: division noise measurement unit
224: difference image calculation unit

The invention claimed is:
1. An X-ray CT device comprising:
an X-ray generation unit for generating X-ray;

an X-ray detection unit for detecting the X-ray after transmitting through a subject to acquire measured projection data;

an image-taking unit that includes a mechanism provided with the X-ray generation unit and the X-ray detection unit, and rotates around the subject; and an image generation unit that includes an iterative approximation reconstruction unit for iteratively correcting a CT image generated by the image-taking unit from the measured projection data so as to substantially equalize a difference between calculated projection data acquired by a forward projection calculation from the CT image and the measured projection data, wherein the image generation unit includes a table unit that stores a relationship between a noise or an X-ray reduction ratio of the CT image and a parameter used for iterative correction, the iterative approximation reconstruction unit determines the parameter from the table unit in accordance with the noise or the X-ray reduction ratio of the CT image, the iterative approximation reconstruction unit includes a weight calculation unit for calculating a weight used for iteratively correcting the CT image from the measured projection data, and determines the parameter from the table unit in accordance with the weight calculated by the weight calculation unit, the weight calculation unit calculates a ratio between a reference weight $W_b$ as a value derived from summing the weight of at least one of a plurality of detection elements which constitute the X-ray detection unit under at least one image-taking condition, at least one reconstruction condition, and at least one reference position, and a weight $W_I$ as a value derived from summing the weight of at least one detection element under conditions other than the image-taking condition, the reconstruction condition, or at a position other than the reference position, and the iterative approximation reconstruction unit determines the parameter under conditions other than the image-taking condition, the reconstruction condition, or at the position other than the reference position from a parameter of the reference weight $W_b$ and the calculated ratio between the weights $W_b$ and $W_I$.

2. The X-ray CT device according to claim 1, wherein:

the weight calculation unit calculates a weight set as a constant value for adding the same weight to output data of the plurality of detection elements; and the iterative approximation reconstruction unit determines the parameter from the ratio between the reference weight $W_b$ calculated from the weight set as the constant value, and the weight $W_I$ as a value derived from summing weights each set as the constant value of at least one detection element under conditions other than the image-taking condition, the reconstruction condition, or at the position other than the reference position.

3. The X-ray CT device according to claim 1, wherein:

the weight calculation unit calculates the weight set as a constant value for adding the same weight to the output data of the plurality of detection elements, and a weight of a statistic value which makes the weight added to the output data of the plurality of detection elements different in accordance with an output volume of the plurality of detection elements; and the iterative approximation reconstruction unit determines the parameter from the ratio between the reference weight $W_b$ calculated from the weight set as the constant value and the weight $W_I$ of the statistic value.

4. The X-ray CT device according to claim 1, wherein the weight calculation unit calculates the ratio between the weights $W_b$ and $W_I$ by using the representative weight $W_b$ with the shortest distance among the two or more reference weights for the parameter at the position other than the reference position.

5. The X-ray CT device according to claim 1, wherein the iterative approximation reconstruction unit determines the parameter from the table unit in accordance with a value acquired from the CT image.

6. The X-ray CT device according to claim 5, wherein the iterative approximation reconstruction unit determines the parameter in accordance with a noise value measured from the CT image so as to acquire a desired noise image from the table unit.

7. The X-ray CT device according to claim 1, wherein the iterative approximation reconstruction unit determines the parameter from the table unit in accordance with an input image-taking condition or the reconstruction condition.

8. The X-ray CT device according to claim 1, wherein the iterative approximation reconstruction unit determines the parameter from the table unit in accordance with subject information acquired from the CT image.

9. The X-ray CT device according to claim 8, wherein the iterative approximation reconstruction unit determines the parameter from the table unit in accordance with weights of the two or more detection elements.

10. The X-ray CT device according to claim 9, wherein the iterative approximation reconstruction unit subjects the weights of the two or more detection elements to fitting with an approximation function, and determines the parameter from the table unit in accordance with an acquired coefficient of the approximation function.

* * * * *